United States Patent
Douglas et al.

(10) Patent No.: US 12,076,719 B2
(45) Date of Patent: Sep. 3, 2024

(54) MICROFLUIDIC CONTACTLESS DEP SEPARATION AND ASSAY SYSTEM

(71) Applicant: Virginia Tech Intellectual Properties, Inc., Blacksburg, VA (US)

(72) Inventors: Temple Douglas, Blacksburg, VA (US); Philip Melvin Graybill, Blacksburg, VA (US); Rafael Davalos, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 994 days.

(21) Appl. No.: 16/980,362

(22) PCT Filed: Mar. 12, 2019

(86) PCT No.: PCT/US2019/021941
§ 371 (c)(1),
(2) Date: Sep. 11, 2020

(87) PCT Pub. No.: WO2019/178163
PCT Pub. Date: Sep. 19, 2019

(65) Prior Publication Data
US 2021/0370292 A1    Dec. 2, 2021

Related U.S. Application Data

(60) Provisional application No. 62/641,447, filed on Mar. 12, 2018.

(51) Int. Cl.
*B01L 3/00*   (2006.01)
*B03C 5/00*   (2006.01)
(Continued)

(52) U.S. Cl.
CPC ..... *B01L 3/502715* (2013.01); *B01L 3/50273* (2013.01); *B01L 3/502761* (2013.01);
(Continued)

(58) Field of Classification Search
None
See application file for complete search history.

(56) References Cited

U.S. PATENT DOCUMENTS

| | | | |
|---|---|---|---|
| 2003/0009101 A1* | 1/2003 | Sunagawa | A61B 5/02007 600/437 |
| 2014/0339088 A1 | 11/2014 | Schmelz et al. | |
| 2015/0247820 A1* | 9/2015 | Davalos | B03C 5/005 204/601 |

OTHER PUBLICATIONS

Čemažar, Jaka et al. "Enhanced contactless dielectrophoresis enrichment and isolation platform via cell-scale microstructures." Biomicrofluidics vol. 10,1 014109. Jan. 19, 2016, doi:10.1063/1.4939947 (Year: 2016).*

(Continued)

*Primary Examiner* — P. Kathryn Wright
*Assistant Examiner* — Curtis A Thompson
(74) *Attorney, Agent, or Firm* — Carin R. Miller, Esq.; Johnson, Marcou, Isaacs & Nix, LLC

(57) ABSTRACT

Described herein are aspects of a microfluidic separation and assay system that can include a microfluidic contactless dielectrophoretic (cDEP) device, a microfluidic concentrator, and a microfluidic assay chamber. In some aspects, microfluidic separation and assay system can be included on a single microfluidic chip. Also described herein are methods of using the microfluidic separation and assay system described herein.

20 Claims, 23 Drawing Sheets

(51) Int. Cl.
     B03C 5/02      (2006.01)
     G01N 33/50     (2006.01)
(52) U.S. Cl.
     CPC ............ B03C 5/005 (2013.01); B03C 5/026
           (2013.01); G01N 33/5008 (2013.01); B01L
               2300/0645 (2013.01); B01L 2300/069
           (2013.01); B01L 2300/0829 (2013.01); B01L
               2300/0883 (2013.01); B01L 2400/0424
                 (2013.01); B03C 2201/26 (2013.01)

(56)                References Cited

OTHER PUBLICATIONS

Lewpiriyawong et al. "Continuous sorting and separation of microparticles by size using AC dielectrophoresis in a PDMS microfluidic device with 3-D conducting PDMS composite electrodes". Electrophoresis. 2010;31(15):2622-2631. (Year: 2010).*
Hu X, Bessette PH, Qian J, Meinhart CD, Daugherty PS, Soh HT. Marker-specific sorting of rare cells using dielectrophoresis. Proc Natl Acad Sci U S A. 2005;102(44):15757-15761. (Year: 2005).*
"International Search Report and Written Oppinion for PCT/US2019/021941", issued by the United States Patent and Trademark Office, as International Searching Authority on May 10, 2019.
Salmanzadeh, A. et al., "Microfluidic mixing using contactless dielectrophoresis", Electrophoresis, vol. 32, pp. 2569-2578, Accepted: Jun. 2, 2011.
Sano et al., "Multilayer contactless dielectrophoresis:Theoretical considerations", Electrophoresis, 2012, 33:1938-1946.
N. Picco et al.,"Integrating Models to Quantify Environment-Mediated Drug Resistance", 2017. Cancer Res, 77(19) 5409-5418.
Kurachi et al., "Optimized retroviral transduction of mouse T cells for in vivo assessment of gene function", Nat. Protoc, 2017, 12, 1980-1998.
Pethig, R., "Dielectrophoresis: An assessment of its potential to aid the research and practice of drug discovery and delivery☆", (2010) Biomicrofluidics 4:135. doi10.1063/1.3456626.
Drasdo and Hohme, "A single-cell-based model of tumor growth in vitro: monolayers and spheroids", Phys. Biol., 2005, 2, 133-147.
Jiao and Torquato, "Emergent Behaviors from a Cellular Automaton Model for Invasive Tumor Growth in Heterogeneous Microenvironments". PLoS Comput. Biol., 2011, 7, 1012, 14 pages.
Zhao et al., "Early and multiple origins of metastatic lineages within primary tumors", PNAS 2016, 113, 2140-2145.
Lambert et al., "Bacteria and game theory: the rise and fall of cooperation in spatially heterogeneous environments", Interface Focus, 2014, 12 pages.
Hanahan and Weinberg, "Hallmarks of Cancer: The Next Generation", Cell, 2000, 100, 57-70.
Wu, A. Emergence of chemotherapy resistance in cancer: microenvironments, genomics, and game theory approaches. Dissertation, 2015, 142 pages.
Vermeulen et al., "Defining Stem Cell Dynamics in Models of Intestinal Tumor Initiation", Science (80), 2013, 342, 995-998.
Shafiee et al., "Selective isolation of live/dead cells using contactless dielectrophoresis (cDEP)", (2010) Lab Chip 10:438-445.
Pethig and Kell, "The passive electrical properties of biological systems: their significance in physiology, biophysics and biotechnology", (1987) Phys Med Biol 32:933-970.
Cemazar and Kotnik, "Dielectrophoretic field-flow fractionation of electroporated cells", (2012) Electrophoresis 33:2867-2874.
Wodarz, D., Somatic Evolution of Cells and the Development of Cancer, Biolgical Theory, 1, 2, 2006, 119-122.
Kitano, H., "Tumour tactics", Nature, 2003, 426, 125.
Creekmore et al., "Regulation of Cytoskeleton Organization by Sphingosine in a Mouse Cell Model of Progressive Ovarian Cancer", Biomolecules, 2013, 3, 386-407.

Salmanzadeh et al., "Sphingolipid Metabolites Modulate Dielectric Characteristics of Cells in a Mouse Ovarian Cancer Progression Model", Integr. Biol. (Camb), 2013, 5, 843-852.
Ebos et al., "Accelerated Metastasis after Short-Term Treatment with a Potent Inhibitor of Tumor Angiogenesis", Cancer Cell, 2009, 15, 232-239.
Ross et al., "Contributions of cell kill and posttreatment tumor growth rates to the repopulation of intracerebral 9L tumors after chemotherapy: An MRI study", Proc. Natl. Acad. Sci., 1998, 95, 7012-7017.
Flemming, "What's driving T cell dysfunction?", Nat. Rev. Cancer, DOI:10.1038/nrc2016.139, May 2019, 251.
Tysnes, B.B., "Tumor-Initiating and -Propagating Cells: Cells That We Would Like to Identify and Control", Neoplasia, 2010, 12, 506-515.
Pavesi et al., "Engineering a 3D microfluidic culture platform for tumor-treating field application", Sci. Rep. 2016, 6, 10 pages.
Babahosseini et al., "Biomechanical profile of cancer stem-like/tumor-initiating cells derived from a progressive ovarian cancer model", Nanomedicine Nanotechnology, Biol. Med., 2014, 10, 1013-1019.
Pethig et al., "Dielectrophoresis: A Review of Applications for Stem Cell Research", Biomed Biotechnol., 2010, DOI:10.1155/2010/182581.
Gascoyne and Vykoukal, "Particle separation by dielectrophoresis", (2002) Electrophoresis 23:1973-1983.
Gupta et al., "Stochastic State Transitions Give Rise to Phenotypic Equilibrium in Populations of Cancer Cells", Cell, 2011, 146, 633-44.
Rutledge and Cimini, "Consequences of aneuploidy in sickness and in health", Curr. Opin. Cell. Biol., 2016, 40, 41-46.
Salmanzadeh et al., "Isolation of prostate tumor initiating cells (TICs) through their dielectrophoretic signature", Lab Chip, 2012, 12, 182-189.
Cox et al., "Toward the Broad Adoption of 3D Tumor Models in the Cancer Drug Pipeline", ACS Biomater. Sci. Eng., 2015, 1, 877-894.
Camacho-Alanis et al., "Transitioning Streaming to Trapping in DC Insulator-based Dielectrophoresis for Biomolecules", (2012) Sens Actuators B Chem. 173:668-675.
Lang,et al., Plastic CD34 and CD38 expression in adult B-cell precursor acute lymphoblastic leukemia explains ambiguity of leukemia-initiating stem cell populations», Leukemia (2017) 31, 731-734.
Bonner et al., "Fluorescence Activated Cell Sorting", Rev. Sci. Instrum., 1972, 43, 404-409.
Gangon, Z.R., "Cellular dielectrophoresis: Applications to the characterization, manipulation, separation and patterning of cells", Electrophoresis, 2011, 32, 2466-2487.
Nadine Besse's dissertation, "Large Array of Shape Memory Polymer Actuators for Haptics and Microfluidics", Thèse No. 8175 (2018), 110 pages.
Hankare et al., "Low temperature route to grow polycrystalline cadmium selenide and mercury selenide thin films" (2003) Materials Chemistry and Physics, 82(3), 505-508.
Ivey et al., "Targeted cellular ablation based on the morphology of malignant cells", Sci. Rep., 2015, 5, 17 pages.
Bonakdar et al., "Electroporation of Brain Endothelial Cells on Chip toward Permeabilizing the Blood-Brain Barrier", Biophys. J., 2016, 110, 503-513.
Mutterer and Rasband, "imageJ Macro Language Programmer's Reference guide v1.46d", https://imagej.nih.gov/ij/docs/macro_reference guide, 45 pages.
Kihara et al., "Measurement of Biomolecular Diffusion in Extracellular Matrix Condensed by Fibroblasts Using Fluorescence Correlation Spectroscopy", PLoS One, vol. 8, issue 11, Nov. 2013, 8 pages.
Davoli and de Lange, "The Causes and Consequences of Polyploidy in Normal Development and Cancer", Annul. Rev. Cell Dev. Biol. 27, 585-610 (2011).
Dewhurst, et al., "Tolerance whole of genome doubling propagates chromosomal instability and accelerates cancer genome evolution", Cancer Discov. 4, 175-185 (2014).

(56) References Cited

OTHER PUBLICATIONS

Gusev et al., "Long-Term Dynamics of Chromosomal Instability in Cancer: A Transition Probability Model", Math. Comput. Model. 33, 1253-1273 (2001).
Gascoyne and Shim, "Isolation of Circulating Tumor Cells by Dielectrophoresis", Cancers, 2014, 6, 545-579.
Huang et al., "Introducing Dielectrophoresis as a New Force Field for Field-Flow Fractionation", Biophys. J., 1997, 73, 1118-1129.
Gascoyne et al., "Correlations between the Dielectric Properties and Exterior Morphology of Cells Revealed by Dielectrophoretic Field-Flow Fractionation", Electrophoresis, 2013, 34(7): 1042-1050.
Cemazar et al., Enhanced contactless dielectrophoresis enrichment and isolation platform via cell-scale microstructures, Biomicrofluidics 10, 014109 (2016), 14 pages.
Pethig, "Review Article—Dielectrophoresis: Status of the theory, technology, and applications", Biomicrofluidics 4, 022811 2010, 35 pages.

\* cited by examiner

| | Red Beads | Blue Beads | Output Volume at 2 μl/min |
|---|---|---|---|
| Outlet 1 | 53 | 282 | 8 μl |
| Outlet 2 | 0 | 4 | 8 μl |

FIG. 13

| 12.5% Output Mixture in DI water | Outlet 1 | Outlet 2 |
|---|---|---|
| Trial 1: Chip 1 | 1.46 mS/cm (68% glycosil mix) | 0.33 mS/cm (11% glycosil mix) |
| Trial 2: Chip 1 | 1.71 mS/cm (74% glycosil mix) | 0.46 mS/cm (17% glycosil mix) |
| Trial 3: Chip 2 | 1.72 mS/cm (75% glycosil mix) | 0.68 mS/cm (27% glycosil mix) |
| Trial 4: Chip 2 | 2.2 mS/cm (97% glycosil mix) | 1.24 mS/cm (53% glycosil mix) |

FIG. 15

|  | Cell Type 1 | Cell Type 2 | Cell Type 3 |
|---|---|---|---|
| Growth Rate | 0.2 | 0.1 | 0.05 |
| Treatment Effectiveness | 0.1 | 0.04 | 0.02 |

FIG. 17

MICROFLUIDIC CONTACTLESS DEP SEPARATION AND ASSAY SYSTEM

CROSS-REFERENCE TO RELATED APPLICATIONS

This application is the U.S. National Stage Application under 35 U.S.C. § 371 of Patent Cooperation Treaty Application No.: PCT/US2019/021941, filed on Mar. 12, 2019, entitled "Microfluidic Contactless DEP Separation and Assay System," the contents of which is incorporated by reference herein in its entirety. Patent Cooperation Treaty Application No.: PCT/US2019/021941 claims the benefit of and priority to U.S. Provisional Patent Application No. 62/641,447, filed on Mar. 12, 2018, entitled "Downstream Microfluidic Culture Chamber for a Collagen Migration Assay of Tumor Subpopulations Separated by Contactless Dielectrophoresis," the contents of which is incorporated by reference herein in its entirety.

STATEMENT REGARDING FEDERALLY SPONSORED RESEARCH

This invention was made with Government support 5R21 CA173092-01 awarded by the National Institutes of Health. The Government has certain rights in the invention.

BACKGROUND

Rapidly determining a cellular response to an agent or treatment can be important for drug and other compound development as well as patient diagnosis and treatment. As such, there exists a need for high-throughput screening devices and techniques.

SUMMARY

Described herein are aspects of a microfluidic separation and assay system that can include a microfluidic contactless dielectrophoretic (cDEP) device, wherein the microfluidic cDEP device can include a main chamber. The main chamber can have a main channel layer and an electrode layer, wherein the electrode layer can have electrode channels. The main channel layer and the electrode layer can be separated by a membrane. The main channel can have a plurality of pillars and a cell suspension inlet microchannel, wherein the cell suspension inlet microchannel can be coupled to the main channel layer. The cDEP device can have an electrode buffer inlet microchannel, wherein the electrode buffer inlet microchannel can be coupled to the electrode channel. The microfluidic separation and assay system can also include a microfluidic concentrator, wherein the microfluidic concentrator can be coupled to the microfluidic cDEP device, wherein the microfluidic concentrator has a main chamber. The concentrator main chamber can have a first inlet configured to receive a fluid flow from the microfluidic cDEP device, a second inlet configured to receive an uncured hydrogel; and a porous wall extending diagonally along the length of the main chamber and across the width of the main chamber, wherein the first and the second inlet are on the same side of the porous wall. The concentrator main chamber can also have a first outlet and a second outlet, wherein the first and second outlet are positioned on the end of the main chamber opposite the first and the second inlet, wherein the first outlet and the second outlet are on opposite sides of the porous wall from each other, and wherein the first outlet is on the same side of the wall as the first and the second inlet. The microfluidic separation and assay system can also have an assay chamber, wherein the assay chamber is coupled to the microfluidic concentrator and wherein the assay chamber comprises: a serpentine microchannel comprising an inlet and an outlet, wherein the inlet of the serpentine microchannel is coupled to the first outlet of the main chamber of the microfluidic concentrator via a microchannel; a test microchannel, wherein the test microchannel is positioned relative to the serpentine microchannel such that a fluid flow through the test microchannel is perpendicular to a fluid flow through the serpentine microchannel; and a porous membrane, wherein the porous membrane is positioned between the serpentine microchannel and the test microchannel.

The microfluidic cDEP device, the microfluidic concentrator, and the microfluidic assay chamber can be contained on a single microfluidic chip. The porous wall can have pores having a diameter that is less than the size of a cell. The microfluidic concentrator and the microfluidic assay chamber can include or be made completely of polydimethylsiloxane. The width of the serpentine microchannel can range from about 50 µm to 3 mm. The height of the serpentine microchannel can range from about 50 µm to 1 mm. The main chamber can have about 100 to 20,000 pillars. The electrode channels can be configured to attach to a voltage generator. The porous membrane can have pores that have a diameter that ranges from 0.001 µm to 10 µm.

Also described herein are aspects of a method of using the microfluidic separation and assay system described herein. The method can include suspending cells in a low conductivity buffer to form a cell suspension; adding the cell suspension to the main chamber of the cDEP device via the cell suspension inlet microchannel; adding an electrode buffer to the electrode channel via the electrode buffer inlet; flowing the cell suspension through the main chamber and applying a voltage to the electrode channel to trap at least one cell against at least one pillar; releasing a trapped cell from the pillar; flowing released cells through an outlet of the microfluidic cDEP device into the main chamber of the microfluidic concentrator through the first inlet of the microfluidic concentrator; adding an uncured hydrogel to the main chamber of the microfluidic concentrator; removing the low conductivity buffer from the released cells and uncured hydrogel by passing the low conductivity buffer through the porous wall and out of the main chamber of the microfluidic concentrator through the second outlet of the microfluidic concentrator; removing batches of uncured hydrogel containing the released cells (plugs) from the main chamber of the microfluidic concentrator through the first outlet of the microfluidic concentrator; flowing the plugs into the serpentine microchannel; curing the hydrogel; adding a fluid containing an agent to the testing agent microchannel and allowing the agent to diffuse through the porous membrane and contact at least one cell in the serpentine microchannel. In aspects, the method can further include the step of detecting or measuring a cell response to exposure to the agent. The agent can be selected from the group consisting of an organic chemical compound; an inorganic chemical compound; a biologic; a toxin; an element; or any combination thereof. The low conductivity buffer can be an osmotic pressure balanced solution with conductivity below 300 µS/cm. The electrode buffer can be a high conductivity buffer. The electrode buffer can be a 10× phosphate buffered saline solution. The hydrogel can be selected from the group consisting of: collagen, matrigel, Hystem-C, glycosil, and hyaluronic acid based gels. The voltage applied can range from 0 V to about 500V. The voltage applied can be varied during use. The cells can be obtained from a biopsy.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1A shows a schematic that can compare current biopsy analysis processing techniques (Old Paradigm) and that which can be achieved using the cDEP-migration assay microfluidic device describe herein (New Paradigm). FIG. 1B shows a flowchart that can show aspects of a CDP-migration assay microfluidic process as substantially described herein.

FIGS. 10A-10C can show experimental results of cells in low-density collagen (about 2 mg/mL) flowing through the device. Mixing boundary is shown after 5 minutes of green cells flowing into device at 10 nl/min (after red cells were flown through). (FIG. 10A) Microscope image with long exposure. (FIG. 10B) Bar graph represents red green intensity observed in each column marked in FIG. 10A. Horizontal lines represents background fluorescence for each channel taken from dark areas of image. Boundaries of the channels were excluded due to light reflection off the walls.

(FIG. 12A) Brightfield image of chip made in PDMS (FIG. 12A); (FIG. 12B) Fluorescent beads in the chip when flow at 1 μl/min was paused. (FIG. 12C) Fluorescent beads in the chip when flow at 2 μl/min was paused. Combined brightfield/fluorescent image of outlet with beads flowing into it (FIG. 12D); and Brightfield image of post structure (FIG. 12E).

FIG. 13 shows a table demonstrating the output of chips in a particle tracing experiment.

FIG. 15 shows a table that shows mixing percentages for output buffers.

FIG. 17 shows a table demonstrating growth rate and treatment effectiveness for three cell types.

(FIG. 21A) shows a top view photo and (FIG. 21B) exploded schematic of a cross section across a row of pillars (each 20 μm) with white space added to visually separate layers. The main channel is colored green and contains inlets for both cell suspension and DEP buffer. Electrode channels are colored purple, they are filled with 10×PBS and connected to a high voltage generator. An electric field can be applied across each chamber, perpendicular to the direction of fluid flow.

DETAILED DESCRIPTION

Figure 1A:
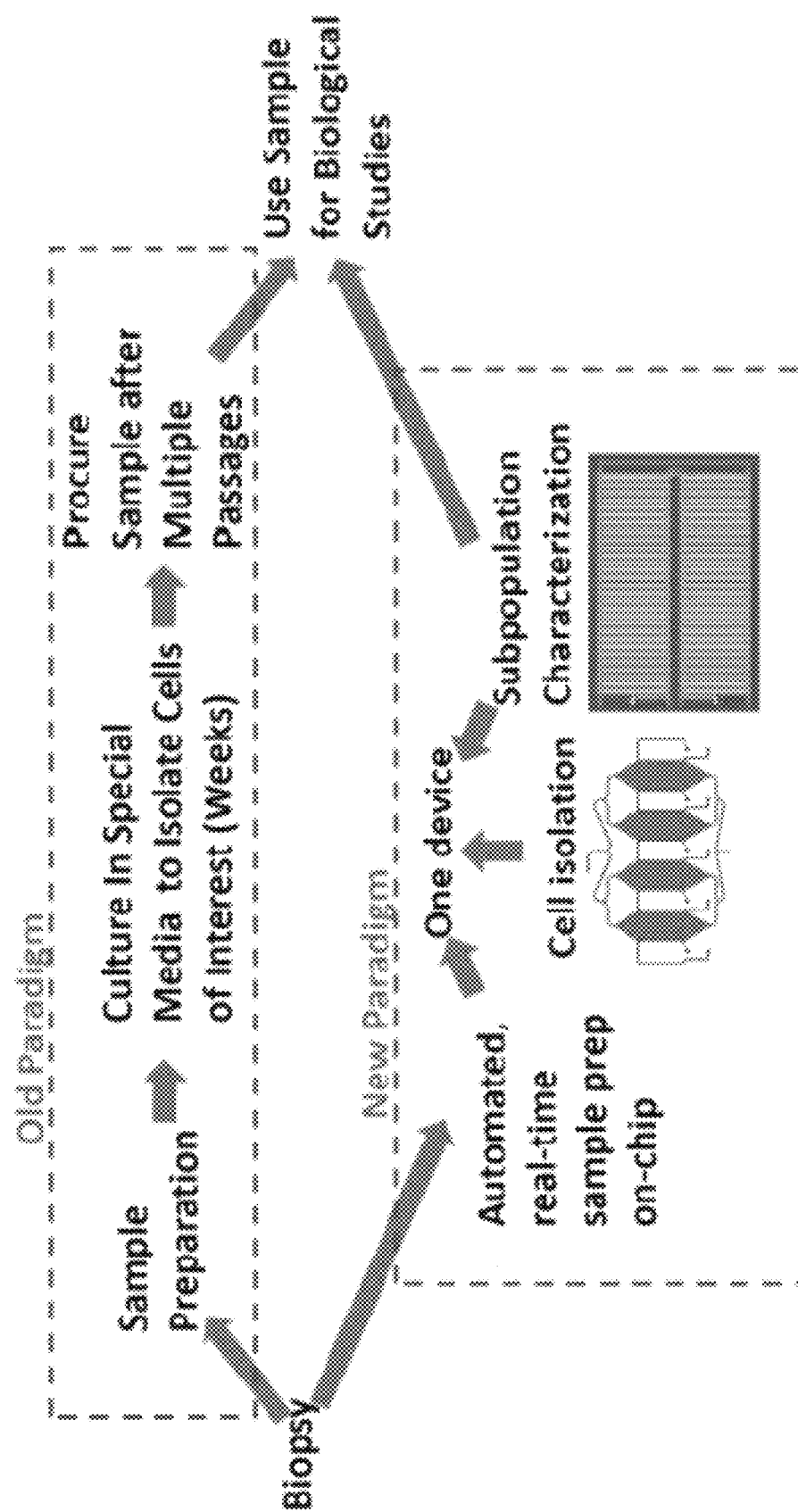
FIGS. 1A-1B show schematic and flowchart of a cDEP-migration assay microfluidic device and process.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, cancer biology, physics, microfluidics, biomedical engineering and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Discussion

Rapidly determining a cellular response to an agent or treatment can be important for drug and other compound development as well as patient diagnosis and treatment. As such, there exists a need for high-throughput screening devices and techniques.

With that said, described herein are aspects of a microfluidic contactless DEP (cDEP) separation and assay system that can be used to screen cells in a high-throughput manner. The microfluidic contactless dielectrophoretic (cDEP) separation and assay system can include a microfluidic cDEP device that can separate populations of cells based on their bioelectric potential, a microfluidic concentrator that can transfer the separated populations of cells to an uncured hydrogel, and a microfluidic assay chamber that can allow rapid exposure of batches of separated cells to be discretely exposed to various agents to allow for measurement and/or detection of cellular responses to the agent(s). Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure. Discussion continues below with a detailed discussion of the various components and aspects thereof of the microfluidic contactless cDEP separation and assay system described herein.

Microfluidic Contactless DEP Device

The microfluidic contactless DEP (cDEP) device described herein can utilize insulating pillars (or posts) to distort the electric filed in order to trap cells of interest. See FIGS. 21A-21B. The microfluidic contactless cDEP device can have one or more microfluidic chambers that can have a width, a length, and volume. The width can range from about 50 μm to about 1 cm. The pillar width can range from 1 μm to 500 μm, although currently we use 20 μm. The width can be uniform through the entirety or the width can vary at one or more points. For example in some aspects, the ends can be tapered such that the width in these regions decrease along a length. The length of the chamber can be measured along the axis of fluid flow. The length of the chamber can range from about 5 mm to about 30 mm. The depth (or height) of the chamber, can range from about 20 μm to about 100 μm. The volume of the chamber can range from about 0.005 μL to 300 μL. One or more microchannels can be coupled to one end of the chamber at a point referred to as the inlet of the chamber. A microchannel can serve as an inlet microchannel for a fluid containing cells (e.g. a cell suspension). The fluid that the cells are in can be a low conductivity buffer. The low conductivity buffer can have a conductivity that ranges from 20 μS/cm to 300 μS/cm. A microchannel can serve as an inlet for a DEP buffer, which can be fed only into the electrode channels. The electrode channel(s) can be coupled to a voltage generator. The voltage generator can be a high voltage generator or a low voltage generator. A DEP buffer can be a high conductivity buffer, with conductivity measurements above 1 mS/cm. In some aspects, the high conductivity buffer can be 10× phosphate buffered saline.

Figures 21A, 21B:
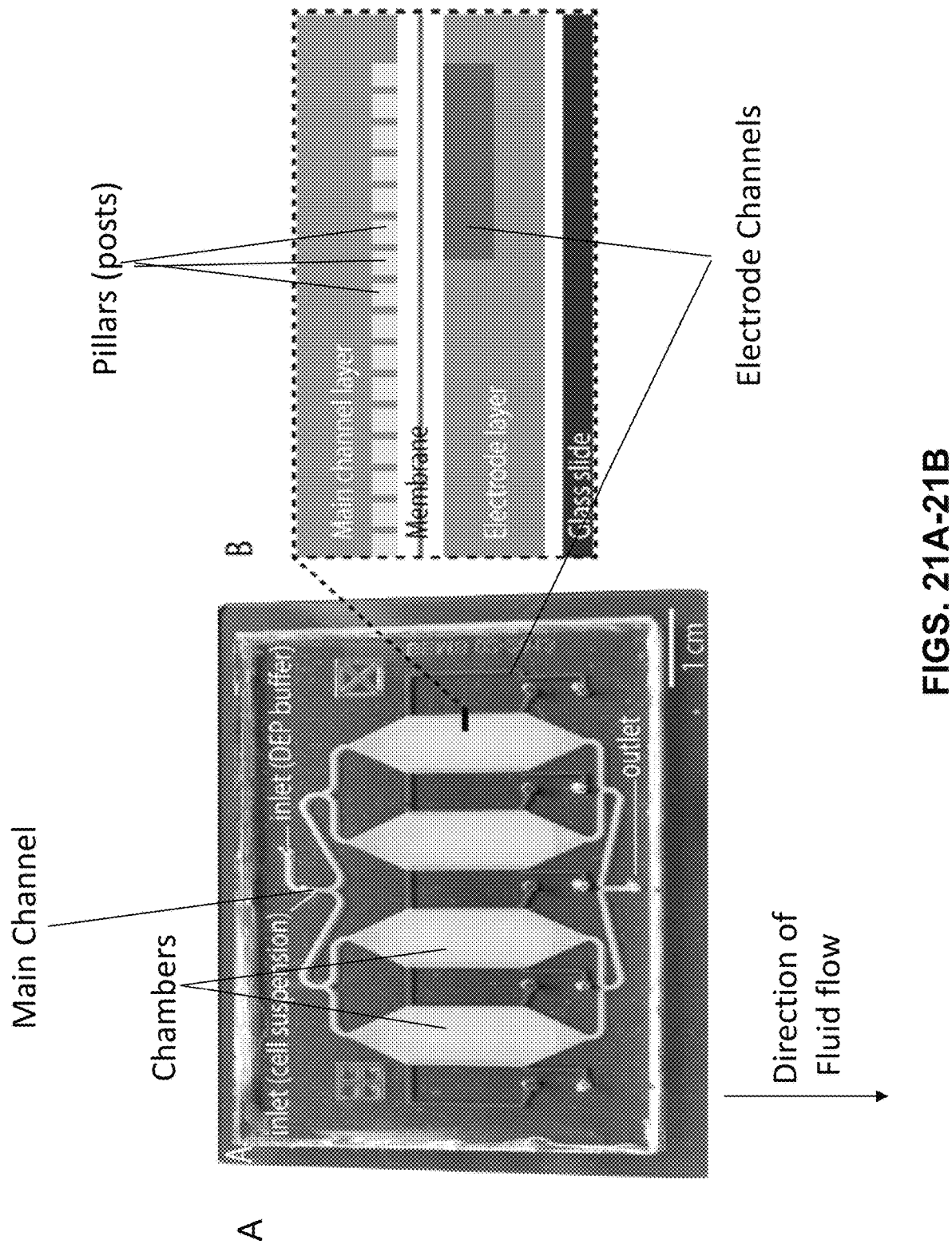
FIGS. 21A-21B shows aspects of a contactless microfluidic dielectrophoresis device.

As shown in FIG. 21B a membrane, which is specific to cDEP, can separate the main chamber and electrodes. The membrane can be composed of PDMS or other polymers such as COC, thermoplastic polymers, and any other nonporous material with low conductivity. The electric field has to penetrate the thin membrane capacitively, which can depend on material, thickness of the membrane, and its surface (M. B. Sano, A. Salmanzadeh, and R. V. Davalos, Electrophoresis 33, 1938 (2012)). The membrane can negate electrochemical damage such as electrolysis and minimizes electroosmosis with the sample. The membrane can have a thickness that can range from about 10 μm to about 20 μm.

Each chamber can have a plurality of pillars that are capable of trapping individual or pairs of cells on the pillar while maintaining high-throughput. Each chamber can have 100 to 1000, 2000, 3000, 4000, 5000, 6000, 7000, 8000, 9000, 10000, 11000, 12000, 13000, 14000, 15000, 16000, 17000, 18000, 19000, 20000 pillars or any number or range of numbers within. Each pillar can have a diameter about the size of a cell, which can generate small trapping regions and minimize cell-to-cell reactions. In some aspects, the pillars can have a diameter or cross-sectional width (if not round) of about 1, to 5, 10, 15, 20, 25, 30, 35, 40, 45, 50, 65, 70, 75, 80, 85, 90, 95, or about 100 μm or any value or range of values within. The pillars can extend upwards from the membrane layer within the main chamber layer of the chamber. The pillars can be made of PDMS, COC, thermoplastic polymers, or any other nonporous and insulative material. Additional aspects of a microfluidic cDEP device can be found in M. B. Sano, A. Salmanzadeh, and R. V. Davalos, Electrophoresis 33, 1938 (2012), which is incorporated by reference as if expressed in its entirety.

The chambers and/or electrode channels and/or main or other microfluidic channels of the microfluidic cDEP device can be made by any suitable method in the art, such as any molding or 3-D printing technique. Microchannels and chambers can be voids having 3 or more walls and can be within a substrate material as shown in FIG. 21A. Such fabrication and design techniques are generally known in the art.

Microfluidic Concentrator

Figure 2:
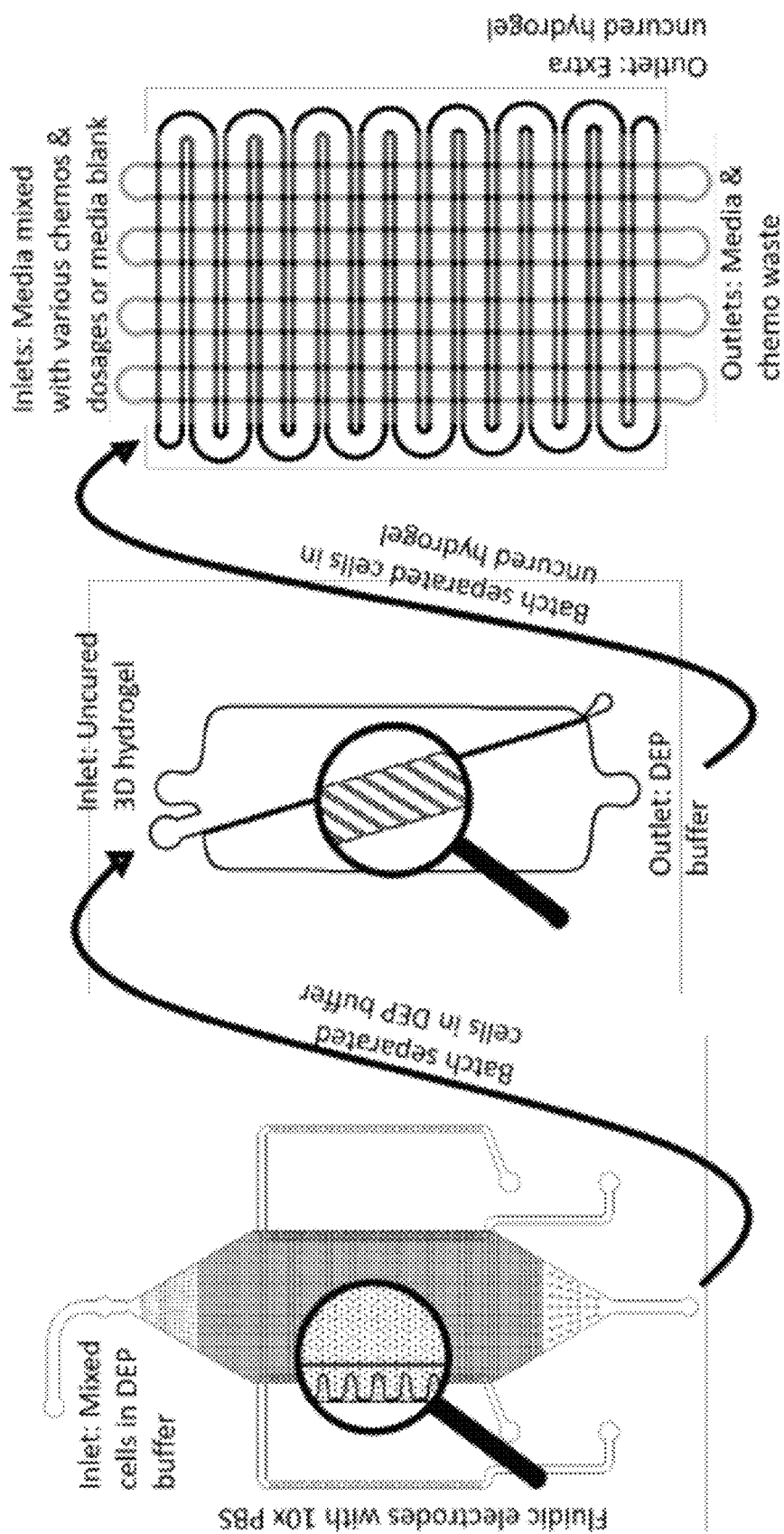
FIG. 2 shows a schematic that can show separation and culture process of the cDEP-migration assay microfluidic device described herein. Mixed cell subpopulations first flow into a device with 20 μm diameter posts. Fluidic electrodes filled with highly conductive phosphate buffered saline at ten times physiological concentration can be used to apply an electric field across the device. Cells in response to the electric field trap on posts based on their unique electrical phenotype, while untrapped cells are washed out. When voltage is turned off, trapped cells are also washed out, resulting in plugs of different phenotypes of cells downstream. These cells then run into a concentrator, where a wall of 7.5 μm pores siphons off the DEP buffer and pushes cells into uncured 3D hydrogel. This hydrogel and cell mixture, still in batches, runs into a downstream chamber where the hydrogel with cells is then cured in distinct subpopulations. An array of buffers can be diffused into the channel across a membrane with 0.4 μm pores. Information from this device, including cell morphology in hydrogel as an indicator of aggressiveness, growth rate and response to chemotherapy or other small molecules diffused across the pores can be fed into a computer optimization model to determine the effect of combinatorial therapy on a theoretical solid tumor containing these subpopulations.
Figure 11:
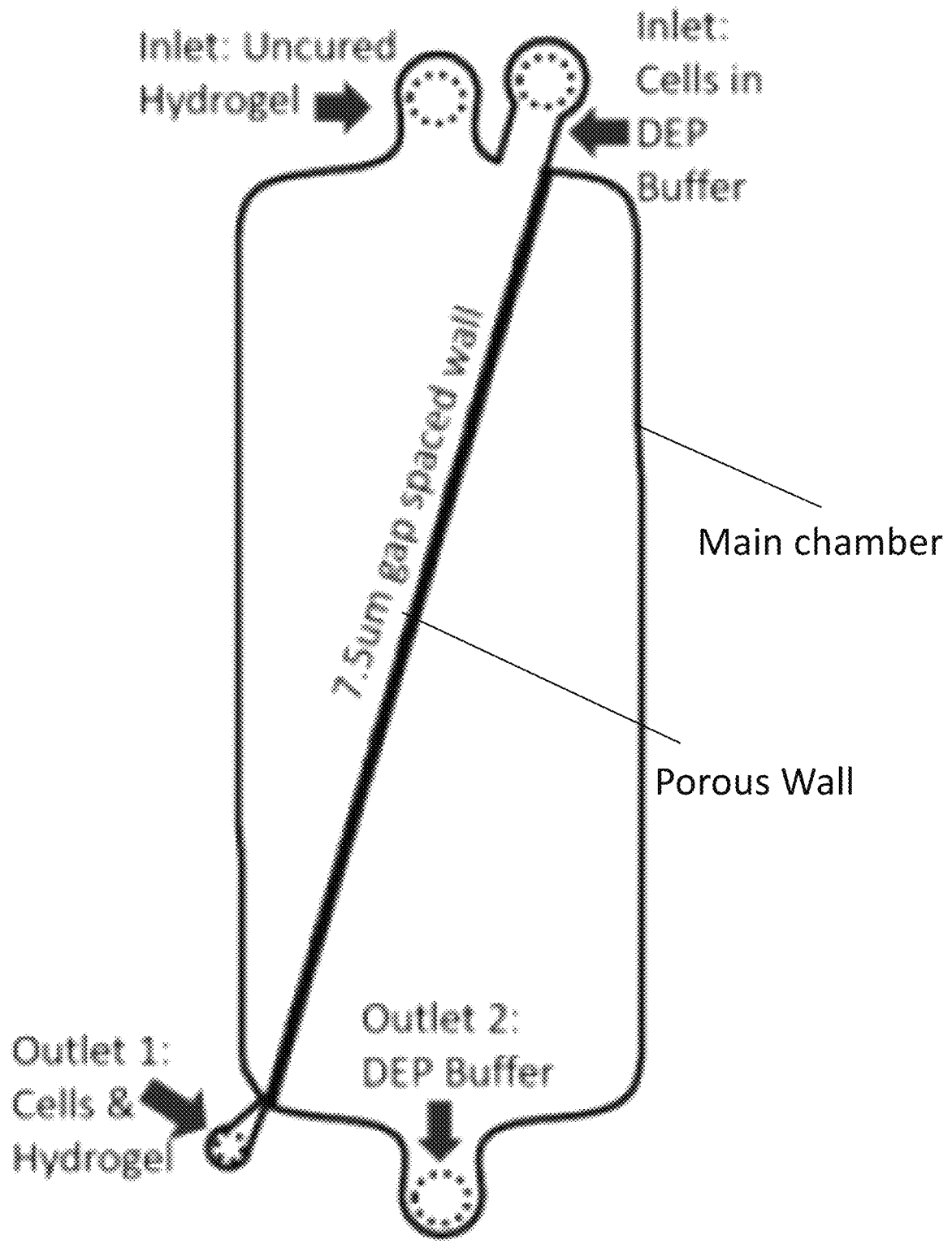
FIG. 11 shows a schematic of a concentrator with labeled chip regions showing punch holes (dotted lines), gap spaced wall, inlets and outlets.
Figure 12D:
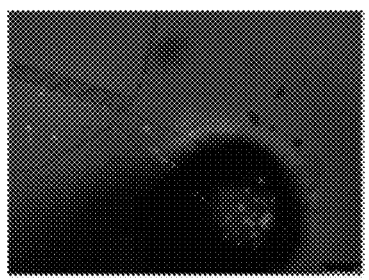
FIGS. 12A-12E show concentrator image.
Figure 12E:
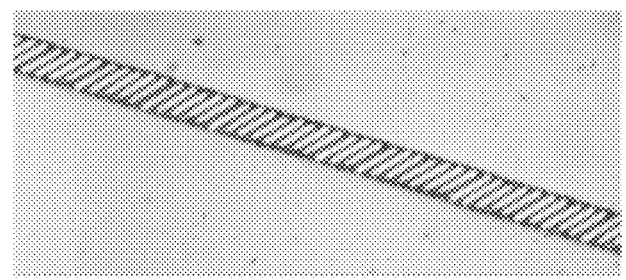
Figure 12C:
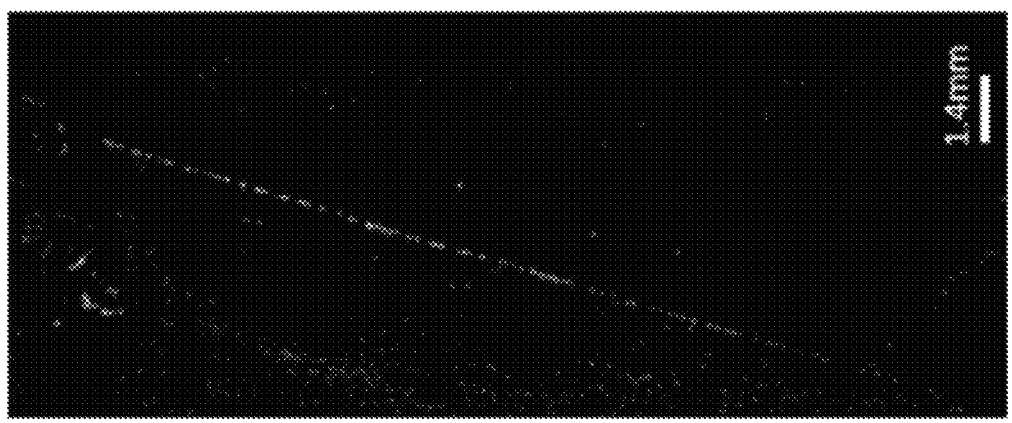
Figure 12B:
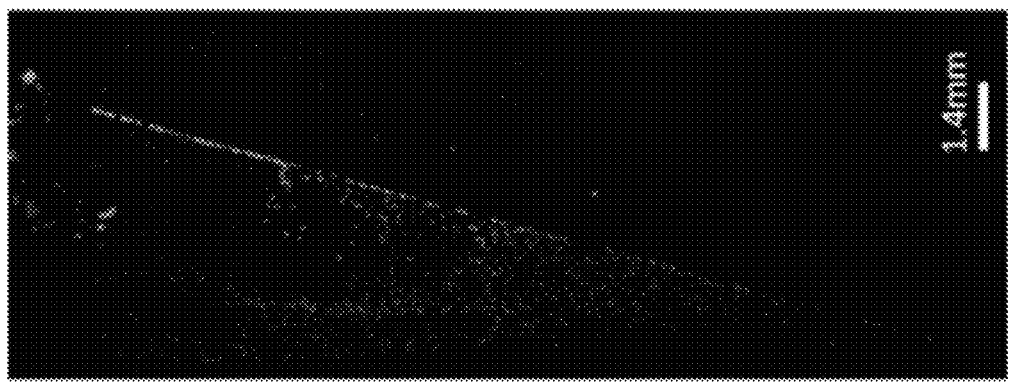
Figure 12A:
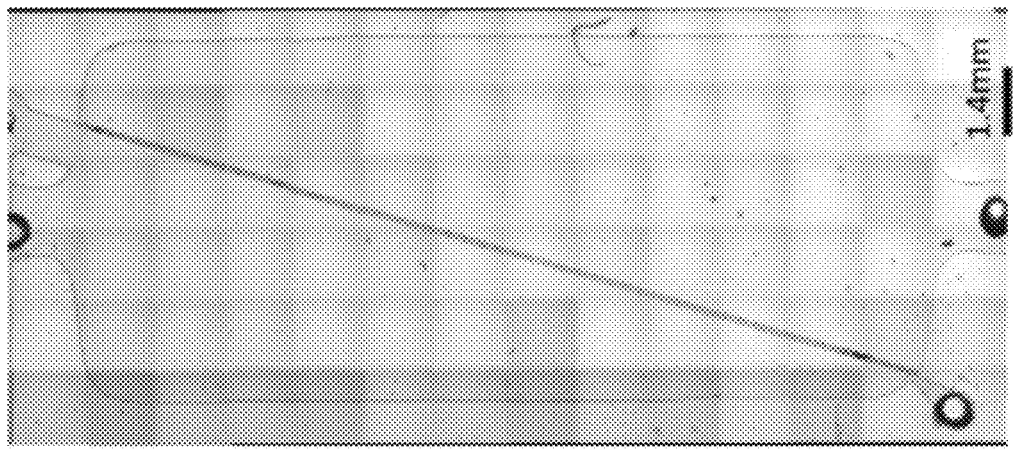

The microfluidic cDEP separation and assay system can also include a microfluidic concentrator (see e.g. FIGS. 2 and 11). The microfluidic concentrator can be in fluidic communication with the microfluidic cDEP device previously described. In some aspects, a microfluidic channel is coupled to an outlet of the microfluidic cDEP device and an inlet of the microfluidic concentrator (e.g. the inlet for cells in DEP buffer of FIG. 11). The microfluidic concentrator can be configured to concentrate the cells in a smaller amount of low conductivity DEP buffer, while simultaneously exchanging the low conductivity buffer used in the DEP separation within the DEP device with an uncured hydrogel. Suitable hydrogels can include, but are not limited to collagen, Hystem-C, matrigel, Glycosil, hyaluronic acid based gels. As shown in FIG. 11, the microfluidic concentrator can include a main chamber with inlets for uncured hydrogel and cells/DEP buffer from the microfluidic cDEP device. The microfluidic concentrator can also include an outlet for cells and uncured hydrogel and an outlet for used DEP buffer. The microfluidic concentrator can also include a porous wall that can be a wall having pores that runs diagonally across the length of the main chamber and function as a sieve. At the inlet end, both inlets are on the same side of the porous wall. At the outlet end, the outlet for the cells/uncured hydrogel and the outlet for the used DEP buffer are on opposite sides of the porous wall. The pores can range in diameter from about 1 μm to about 5 μm. The size of the pores prevents cells from passing through the wall and forces cell to move along the edge of the porous wall into the cell/uncured hydrogel outlet. This wall can be made out of PDMS, COC, thermoplastics, silicon, glass, or any other material capable of printing smooth patterns at this scale. Because the porous wall has a higher net cross-sectional area than a secondary outlet, the low conductivity DEP buffer exits the device while the cells are mixed into the hydrogel before reaching the outlet. The concentrator allows the microfluidic cDEP separation and assay system to be fully microfluidic, avoiding cumbersome centrifugation steps in order to move the cells from DEP buffer to hydrogel, and potentially compromising sterility.

The main chamber of the concentrator that can have a width, a length, and volume. The width can range from about 1 mm to about 150 mm. The width can be uniform through the entirety or the width can vary at one or more points. For example in some aspects, the ends can be tapered such that the width in these regions decrease along a length. The length of the chamber can be measured along the axis of fluid flow. The length of the chamber can range from about 5 mm to about 20 mm. The depth (or height) of the main concentrator chamber, can range from about 10 μm to about 200 μm. The volume of the main concentrator chamber can range from about 7.5 μL to 600 μL.

The chamber, inlets, outlets or other microfluidic channels of the microfluidic concentrator can be made by any suitable method in the art, such as any molding or 3-D printing technique. Microchannels and chambers can be voids having 3 or more walls and can be within a substrate material. Such fabrication and design techniques are generally known in the art. The concentrator can be made out of any suitable material, such as PDMS. This wall can be made out of PDMS, COC, thermoplastics, silicon, glass, or any other material capable of printing smooth patterns at this scale.

Microfluidic Assay Chamber

Figure 5:
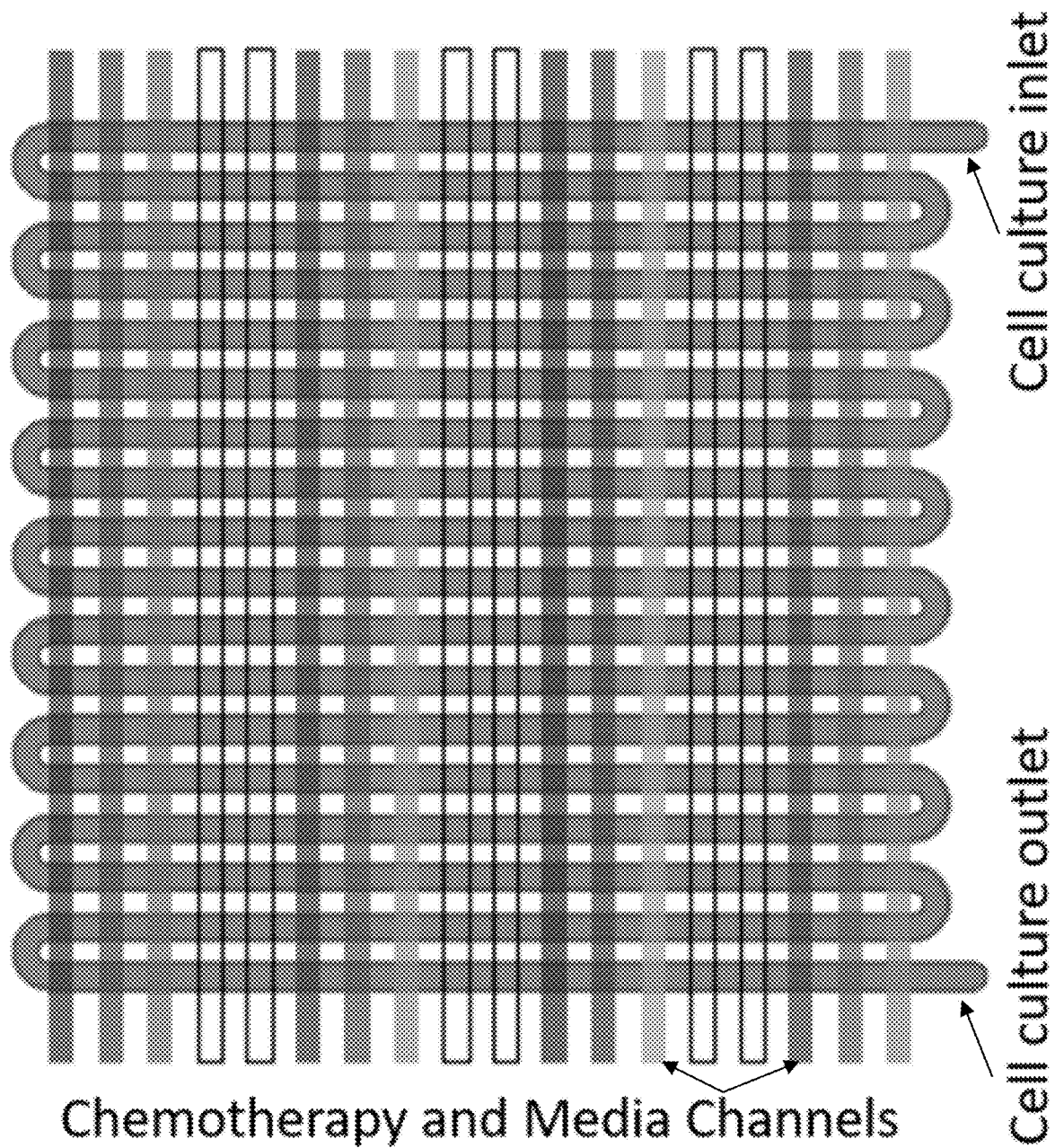
FIG. 5 can show a schematic for serpentine device for multi-subpopulation culturing and analysis.
Figure 16:
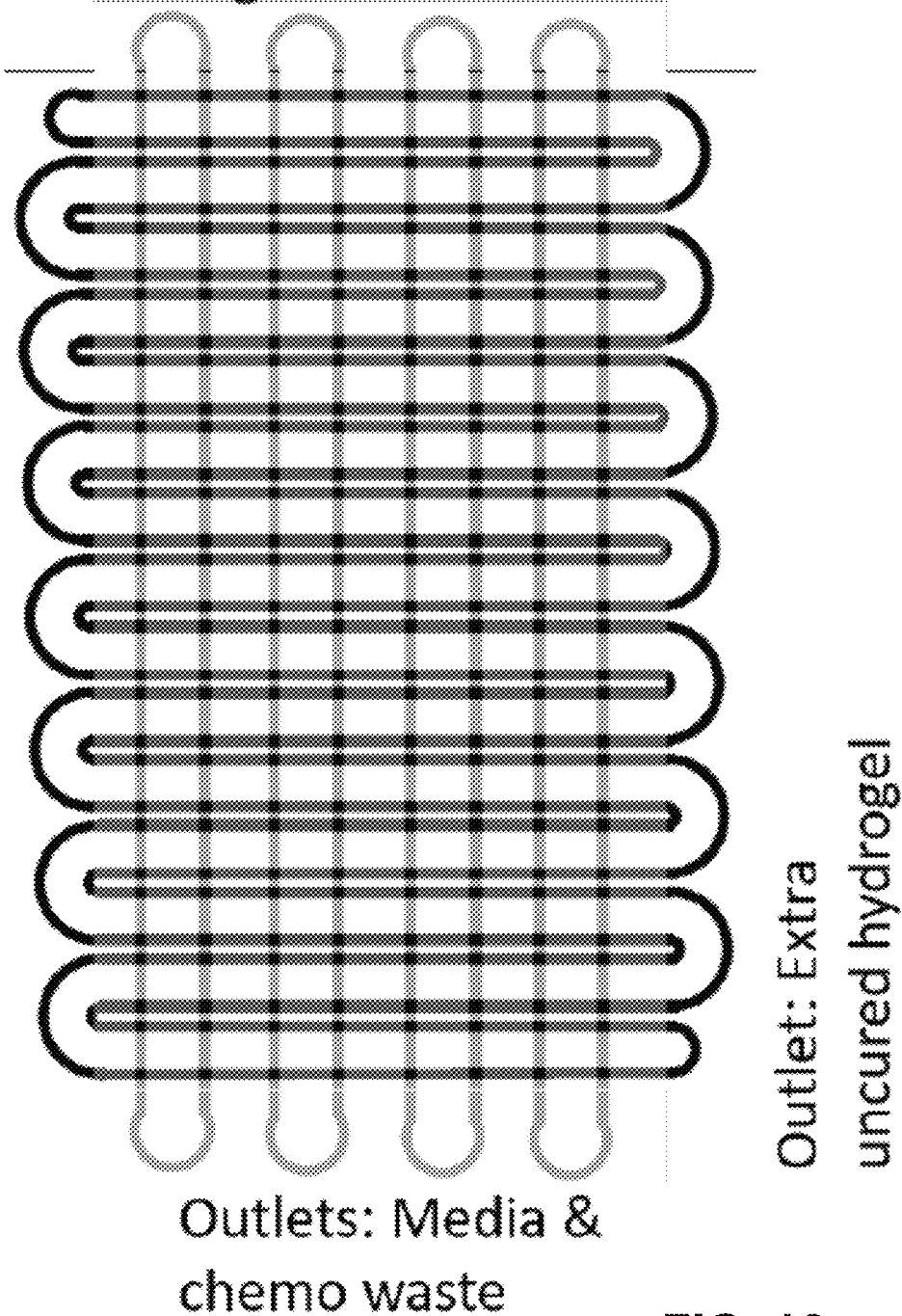
FIG. 16 shows aspects of a serpentine culture chamber for cell subpopulations.

The microfluidic cDEP separation and assay system can also include a microfluidic assay chamber (see e.g. FIGS. 2, 5, and 16). The microfluidic assay chamber can include a serpentine microchannel having a plurality of hairpins. The number of hairpins can range from 1 to 100 or more. The microfluidic assay chamber can be in fluidic communication with the cell/uncured hydrogel outlet of the microfluidic concentrator. A microchannel can couple the cell/uncured hydrogel outlet of the microfluidic concentrator to an inlet of the serpentine microchannel. The width of the serpentine microchannel can range from 50 μm to 3 mm. The height of the serpentine microchannel can range from 50 μm to 1 mm. The total length (from inlet to outlet) of the serpentine microchannel can range from 50 μm to 300 mm. The dimensions of the serpentine microchannel can be optimized to force all the fluid down a single pathway and prevent mixing. As discussed in greater detail below, the uncured hydrogel/cell mix can enter the microfluidic assay chamber as "plugs" which can have a length that is longer than region of mixing, making it easy to distinguish between plugs, particularly when blank buffer is used to space out the plugs.

The microfluidic assay chamber can also include one or more test agent microchannels that can extend across the straight regions of the serpentine microchannel as shown in e.g. FIG. 2. A porous membrane can be placed between the test agent microchannels and the serpentine microchannel to allow diffusible molecules to pass through the membrane and come in contact with cells within the serpentine hydrogel. The pore size of the membrane can range from about 0.001 μm to 10 μm or any value or range of values between.

Once cells in uncured hydrogel are flowed into the serpentine microchannel the hydrogel can cure. Agent(s) can be added to the test agent microchannel(s) and diffused across the membrane to test against the cells within the serpentine microchannel. The test agent microchannels can each have an inlet and an outlet to provide entry of a fluid containing a test agent and to remove used fluid and agent.

Use of the Microfluidic cDEP Separation and Assay System

The microfluidic cDEP separation and assay system can be provided in separate modules (e.g. on separate chips) or can be provided on a single chip. In operation, cells can be suspended in a suitable low conductivity buffer. Suitable low conductivity buffers are described elsewhere herein. Cells can be obtained from any suitable source, including but not limited to, a biopsy, cell culture, or tissue culture. The cells suspension can be applied to an inlet microchannel of the microfluidic cDEP device described elsewhere herein. The cells can be applied in batches with each batch size ranging from about 1 μL to about 100 μL, including any value or range of values within. In some aspects, the batch size is about 50 μL. A voltage can be applied to the main chamber(s) of the microfluidic cDEP device. The voltage can range from 0 V to 500 Vrms. The voltage and frequency can be varied with each batch to collect different subpopulations of cells with each batch based on the bioelectric properties of the cells. Cells are trapped and then released from the pillars based on the voltage applied (or not applied). After release, released cells can then be flowed in the low conductivity buffer through an outlet microchannel and into the concentrator via a concentrator inlet.

Uncured hydrogel can be flowed into the microfluidic concentrator through an uncured hydrogel inlet. The hydrogel can mix with the cells/low conductivity buffer. As previously described, the low conductivity buffer can be separated from the cells/uncured hydrogel and exit the chamber through a buffer outlet. The uncured hydrogel/cell mix can exit the microfluidic concentrator in batches or "plugs". The uncured hydrogel/cell plugs can then be flowed through a connecting microchannel into the serpentine microchannel of the microfluidic assay chamber. There, the hydrogel can be allowed to cure. A fluid containing one or more agents can be added to the test agent microchannel(s) and flowed through the test agent microchannel(s). As the agent containing fluid flows through the test agent microchannel(s), the agent can diffuse across the membrane and come in contact with the cells present in the cured hydrogel. A biologic response of the cells to the agent can then be detected and/or measured.

Any suitable agent can be tested against populations and/or sub populations of cells in this manner. Suitable agents include small molecule therapeutics, biologics, toxins, chemotherapies, nutrient or oxygen or other dissolved gasses and/or gas gradients, DNA, RNA, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and any combination thereof.

The agents can be known agents. Thus, in some aspects, the assays can be used to screen cellular responses to one or more agents. In some aspects, the agents can be unknown. Thus, in some aspects the assays and devices described herein can be used to test unknown samples for the presence of agents based on their effect on various populations of cells with different bioelectric phenotypes.

In some aspects, the microfluidic cDEP separation assay and device can be multiplexed with one or more other upstream assays. In some aspects, the upstream assay can be one that is performed in a multi-well plate. In some aspects, cells from discrete wells can be subjected to a prior assay and then added to the cDEP device for further characterization.

In some aspects, the microfluidic cDEP separation assay and device can be multiplexed with other downstream assays. In some aspects, plugs can be added to wells in a multi-well plate (e.g. a 96-well cell or tissue culture plate). From there additional assays can be performed on the cells. In other embodiments, cells can be collected from the serpentine microchannel after migration through the microchannel and cultured. In some embodiments, culture can be on a multi-well plate (e.g. a 96-well cell or tissue culture plate). From there additional assays can be performed on the cells. In some aspects, microfluidic cDEP device, the microfluidic concentrator, and/or the microfluidic assay chamber are coupled to and/or in fluidic communication with a downstream or upstream multi-well assay system.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Introduction.

Figure 3:
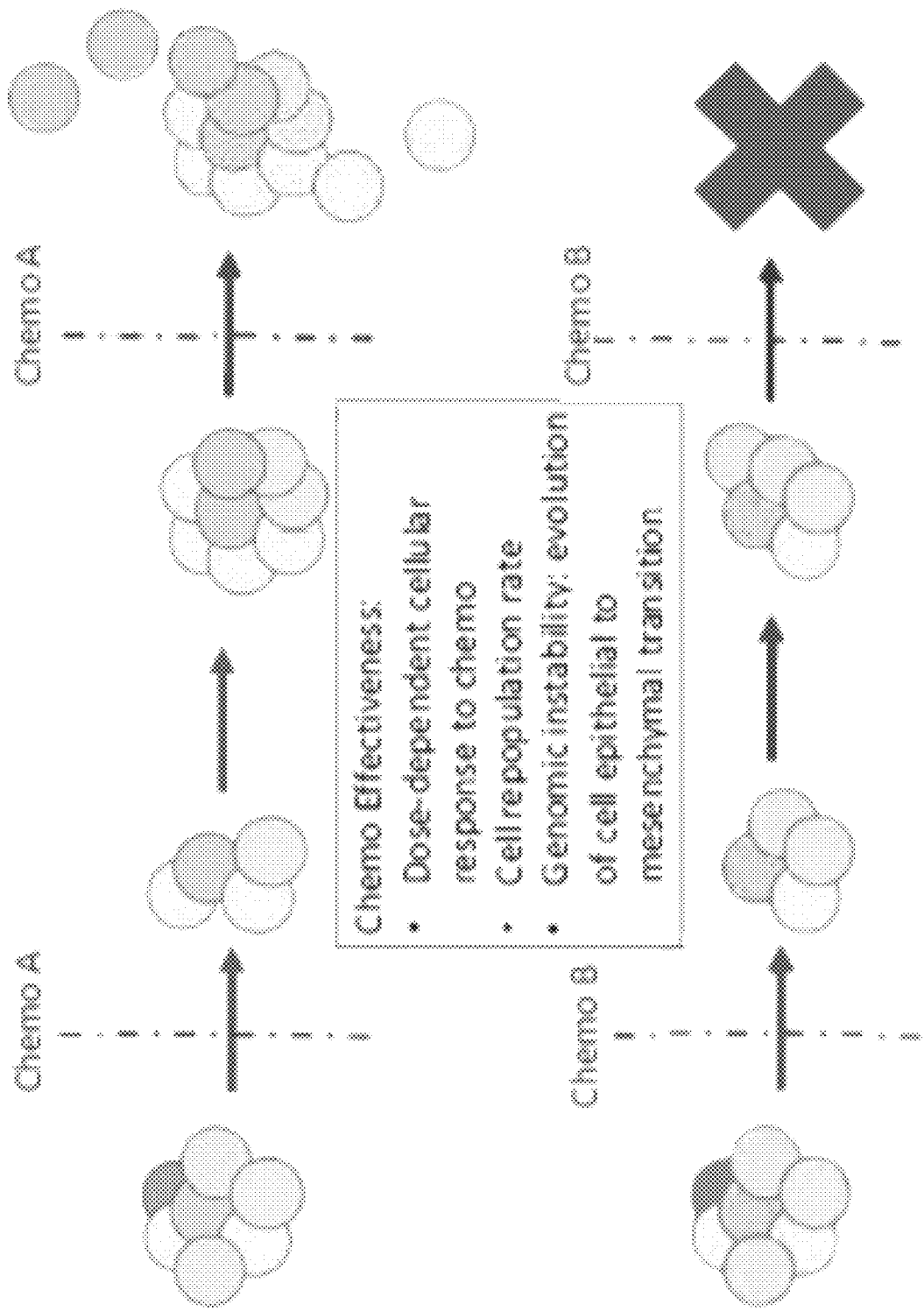
FIG. 3 shows a schematic that can demonstrate how chemotherapy can result in treatment failure.

Cancerous tissue is heterogeneous in nature, often containing several subpopulations of cells with varying degrees of aggressiveness and susceptibility to different types of chemotherapy. Currently, cancer treatment tends to treat the bulk of a tumor, leaving behind treatment-resistant or highly malignant cells that then repopulate the space, leading to treatment-resistance and recurrence. Despite numerous studies, the complexity of determining which treatments will be most effective in different scenarios is still unsolved, with some evidence showing that unoptimized application of chemotherapy can mutate the surviving cells, which can increase heterogeneity and in turn lead to more aggressive and metastatic subpopulation emergence. In particular, attempts to treat metastatic cells often fail, leading to death in many cases. FIG. 3 shows a schematic that can demonstrate how chemotherapy can result in treatment failure.

Figure 1B:
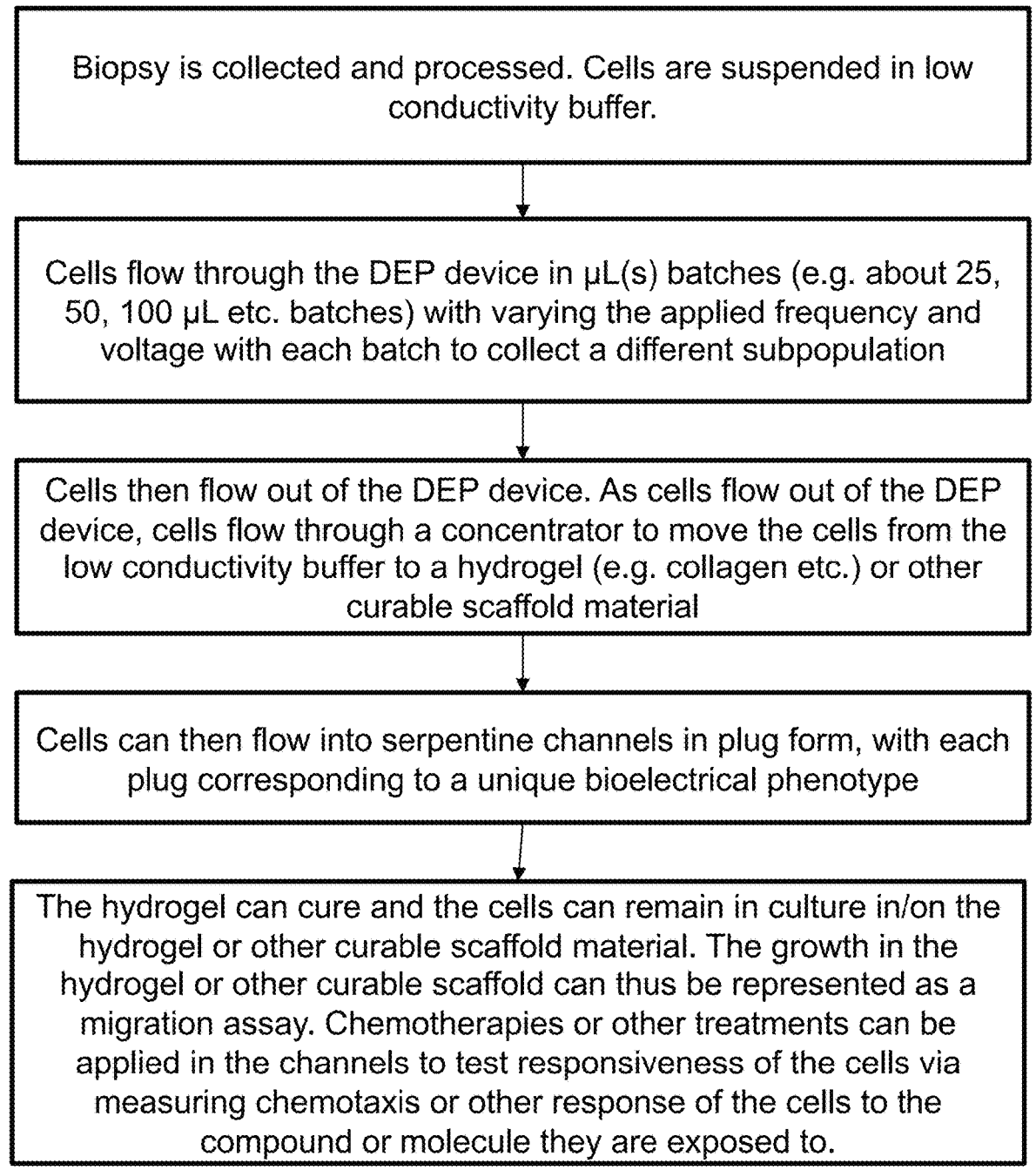

Without being bound by theory, the development of a multistage contactless dielectrophoresis (cDEP) device can improve chemotherapy selection by allowing for morphologically unique cells to be separated based on their electrical polarizability and tested separately against an array of chemotherapies or other therapies (e.g. immune or biologic based therapies). This Example can describe an integrated system for personalized tumor diagnostics, in which each subpopulation in a patient's biopsy is separated by their dielectric signature. Following separation these subpopulations can be moved into a hydrogel aggressiveness assay for characterization and tested against a panel of chemotherapies. This can allow for a more combinatorial approach to be taken to chemotherapy selection, where information on cell aggressiveness, growth rate, and response to chemotherapies can be studied. See e.g. FIGS. 1A-1B.

Prior efforts have shown that it is possible to separate subpopulations of cells within a tumor using dielectrophoresis (DEP). It has been shown that using cDEP, mouse ovarian surface epithelial cells at different stages of malignancy can be separated with DEP, while also retaining high viability. Without limitation, the device described herein can be used as follows: upon receiving a tumor biopsy, cells flow through the dielectrophoretic cell separator where they are separated by their subtype, flow through a system that transfers them to uncured hydrogel, and then flow into a culture chamber where they can be cultured in 3D as an indicator of metastatic capacity. This is followed by testing chemotherapy agents against each cell subtype individually. Using this data (for each subtype, growth rate, malignancy and susceptibility to a panel of chemotherapies or other treatments), we hope to pair this single-chip diagnostic with a computer algorithm that will model optimum treatment regimens based on output data.

Without limitation, the device and/or chip described herein can be used to gather data on the correlation between specific trapping frequencies and regular phenotypic information. We have observed in previous experiments that lower trapping frequency within a cancerous cell type tends to correlate with metastatic capacity, which we hypothesize is due to changes in the structure of the cell membrane before migration. These changes can be observed in the number and form of pseudopodia and in the dysregulation of cell morphology. Current DEP theory does not account for such structural and morphological changes, and with a large database of this information, as well as information on treatment resistance and malignancy, we hope to solve the problem of identifying which cells correlate with specific bioelectrical phenotypes and frequency-dependent states.

Modeling and Theory.

Neutrally charged lossy particles and cells exposed to an inhomogeneous electric field experience a dielectrophoretic force (Eq. 1):

$$\vec{F}_{DEP} = 2\pi\varepsilon_m r^3 ReK(\omega)\nabla|\vec{E}_{rms}|^2 \tag{Eq. 1}$$

Here, r is the radius of the cell, $\vec{E}_{rms}$ is the root mean square of the electric field, is the $\varepsilon_m$ is the permittivity of the medium, and $K(\omega)$ is the Clausius-Mossotti factor. The Clausius-Mossotti factor is describe by Eq. 2, $$(\varepsilon^*_p - \varepsilon^*_m)/(\varepsilon^*_p + 2\varepsilon^*_m) \tag{Eq. 2}$$

where $\varepsilon^* = \varepsilon + i\sigma/\omega$ (Eq. 3), with $\varepsilon^*$ the complex permittivity, $\varepsilon$ the permittivity, $\sigma$ the conductivity, and $I=\sqrt{-1}$ (Eq. 4). The subscripts p and m represent the particle and medium, respectively. The dielectrophoretic force can thus be used to separate cells based upon their radii, the dielectric permittivity of the cells, and the frequency of the applied voltage. By tuning the frequency of the applied voltage, the cDEP chip can attract and trap a subpopulation of the cells to the insulated posts while other subpopulations are repelled [Pethig, Pohl]. In addition to the dielectrophoretic force, cells in a DEP chip also experience the drag force, which balances with this DEP force to optimize trapping [Temple].

Figure 8A:
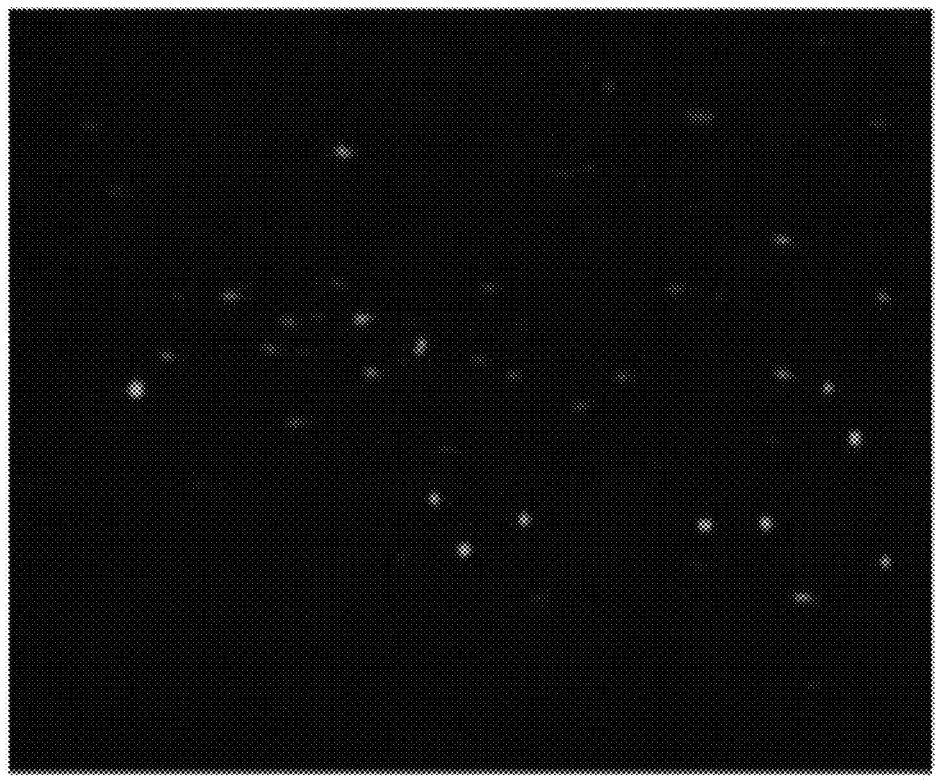
FIGS. 8A-8B can show (FIG. 8A) green cells (fibroblasts) trapped on posts within the chip while red cells (macrophages) are moving through the chip and (FIG. 8B) for the mixed population at 346 Vrms, 1.25 ul/min and 20 kHz, the percentage of macrophages vs. fibroblasts trapped at each point in time is shown.
Figure 8B:
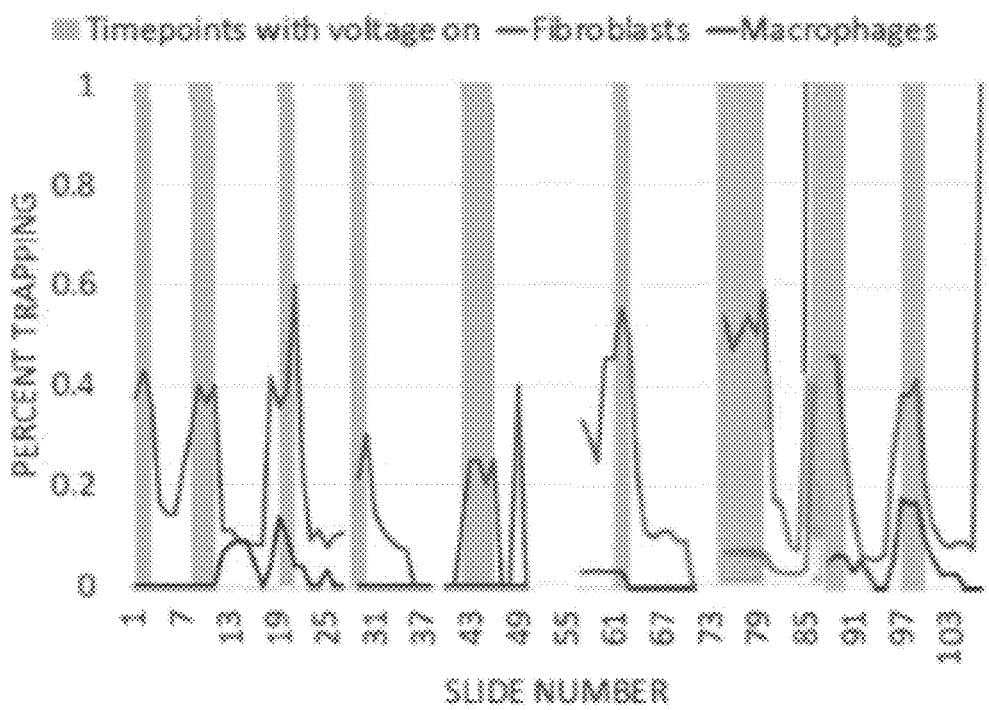

Design: cDEP chip. The microfluidic cDEP chip uses an array of 20 µm PDMS pillars to generate a non-uniform electric field in channel between an applied electric potential. This allows for single cell trapping of cells. In a recent study [temple], we demonstrate that this chip is capable of sorting mouse ovarian surface epithelial cells into subpopulations of aggressive and highly aggressive cells. The specifics of the design and fabrication can be found in previous works [Uaka, Alireza]. For each run, a 50 ul batch of untrapped cells, a 50 ul batch of DEP buffer, and a 50 ul batch of trapped cells was run off the chip and analyzed downstream. FIGS. 8A-8B can show (FIG. 8A) green cells (fibroblasts) trapped on posts within the chip while red cells (macrophages) are moving through the chip and (FIG. 8B) for the mixed population at 346 Vrms, 1.25 ul/min and 20 kHz, the percentage of macrophages vs. fibroblasts trapped at each point in time is shown.

Figure 4:
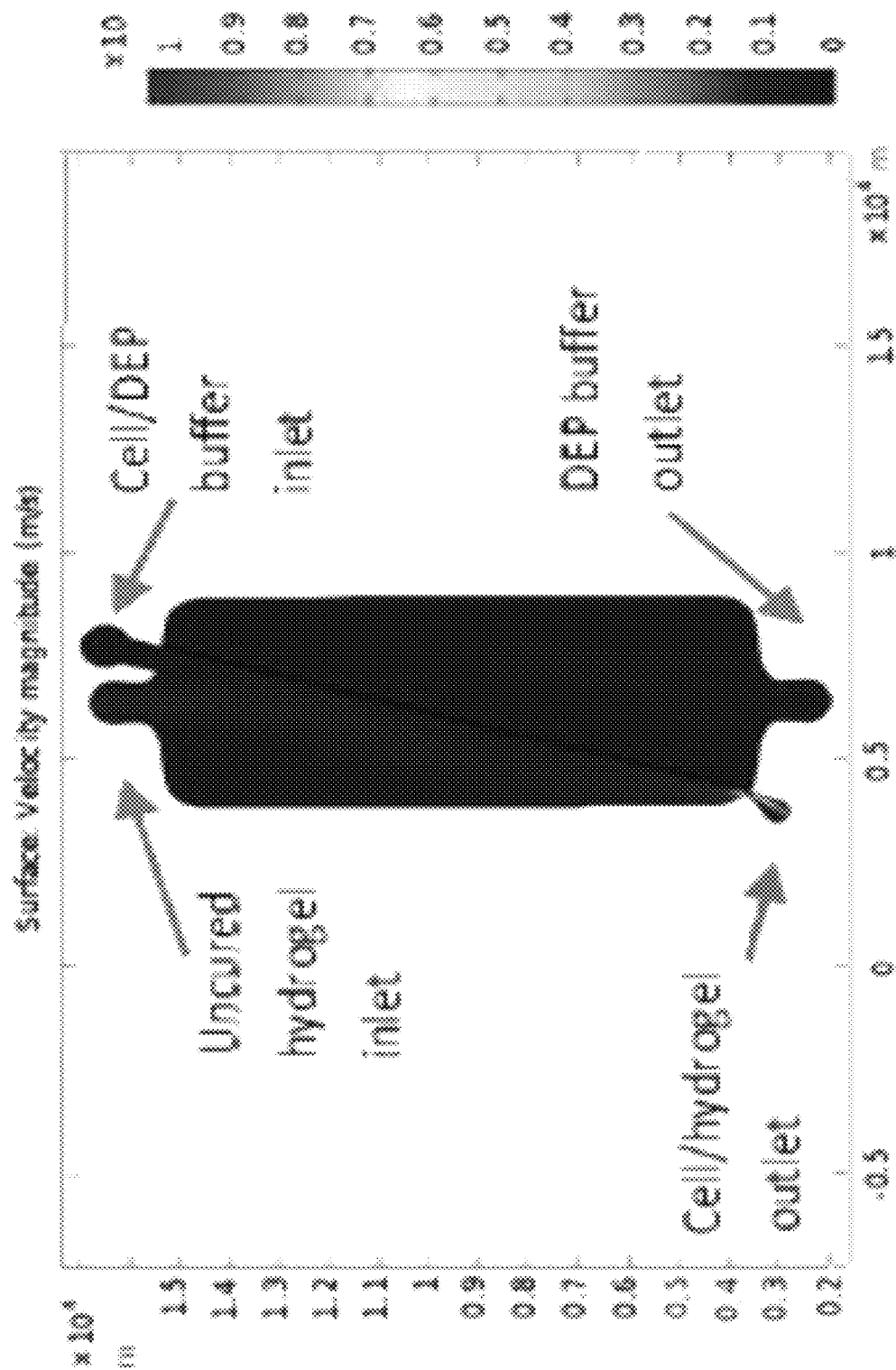
FIG. 4 shows a schematic that can demonstrate pressure driven flow in concentrator section of chip. Cells flow through region of high pressure while DEP buffer is siphoned off through porous wall and replaced with Hystem-C. Wall has 3 micron pores. Collagen inlet: 300 um/s. Cell inlet: 100 um/s.
Figure 6:
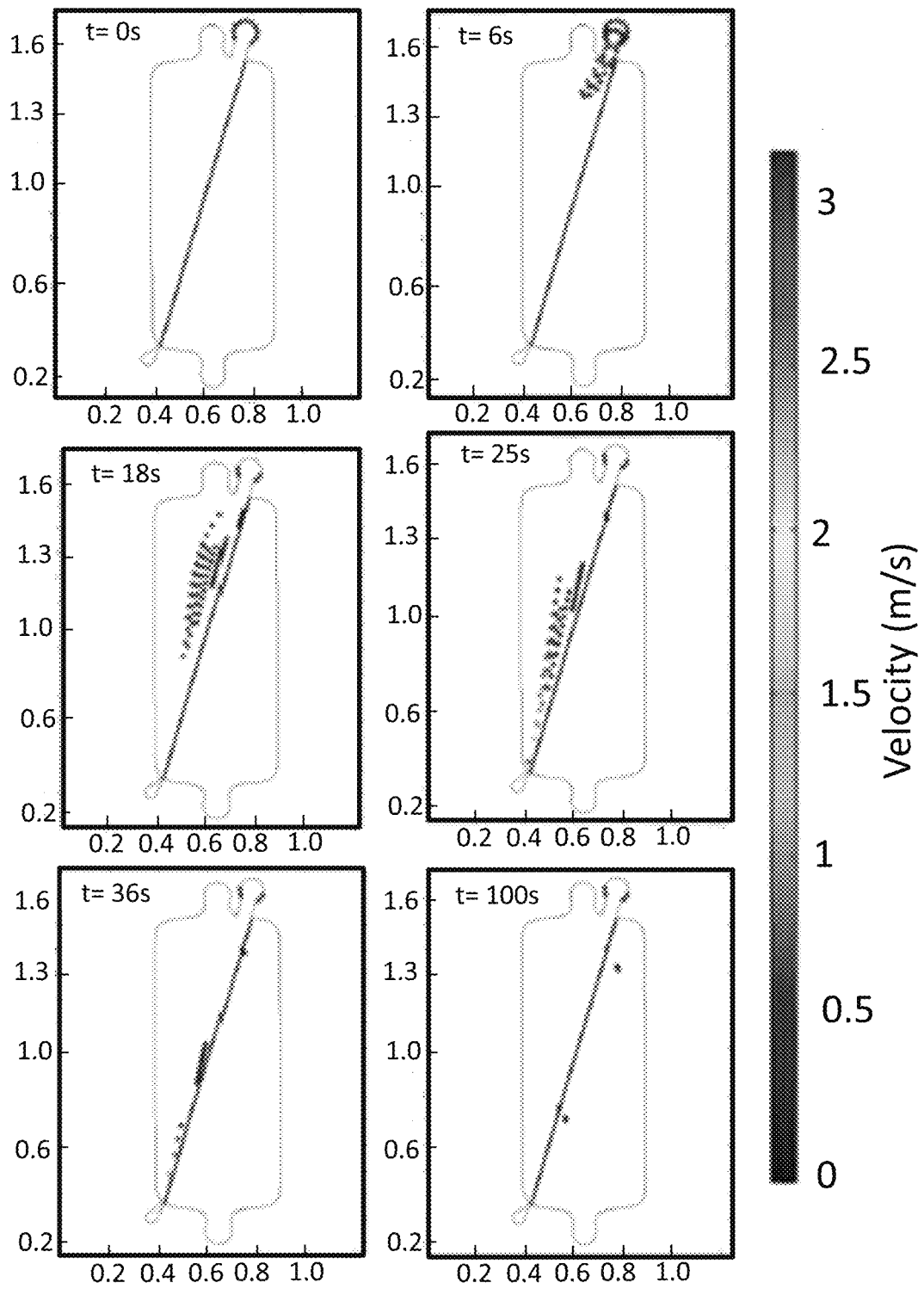
FIG. 6 can show COMSOL particle tracing of cells in the concentrator. Orientation matches that of FIG. 2 lower image. Wall has 3 micron pores. Collagen inlet: 300 μm/s. Cell inlet: 100 um/s. Particle diameter 40 μm.

Design: Cell Concentrator Chip. Located directly downstream of the DEP chip, the cell concentrator was designed to concentrate the cells in a smaller amount of low conductivity DEP buffer while simultaneously exchanging the low conductivity buffer used in the DEP experiments with uncured collagen/hydrogel. This design can accomplish these two tasks using a diagonal wall with small pores that acts as a sieve. As shown in FIG. 2, the small size of the pores prevents cells from passing through the wall and forces cells to move along the edge of the porous wall into an outlet. Because the wall of pores has a higher net crosssectional area than a secondary outlet, the low conductivity DEP buffer exits the device while the cells are mixed into the hydrogel before reaching the outlet. This device allows the system to be fully microfluidic, avoiding cumbersome centrifugation steps in order to move the cells from DEP buffer to hydrogel, and potentially compromising sterility. FIG. 4 shows a schematic that can demonstrate pressure driven flow in concentrator section of chip. Cells flow through region of high pressure while DEP buffer is siphoned off through porous wall and replaced with Hystem-C. Wall has 3 micron pores. Collagen inlet: 300 um/s. Cell inlet: 100 um/s. FIG. 6 can show COMSOL particle tracing of cells in the concentrator. Orientation matches that of FIG. 2 lower image. Wall has 3 micron pores. Collagen inlet: 300 µm/s. Cell inlet: I00 um/s. Particle diameter: 40 µm.

Design: Downstream serpentine 3D culture. Downstream of the cell concentrator, we designed a serpentine channel with optimized width and height so that separated cell populations can flow through the device without mixing. The design forces all the fluid along a single pathway, thus preventing flowrate differences which can occur with a branched channel design. The channel width was made sufficiently narrow so that despite parabolic profile of the cell populations, the length of each plug is much longer than the region of mixing, making it easy to distinguish between plugs, particularly with blank buffer flown between each set of cells. The channel width was made sufficiently wide to avoid significant pressure in the device. This was experimentally optimized. The serpentine channels were modelled in COMSOL with the fluid dynamics module and with particle tracing.

The channels for cell flow are chemotherapy (or other therapy type) channels with the cell serpentine, so that different chemotherapies (or other molecule or agent) can be tested against the cell populations. These are separated by a 0.4 µm permeable membrane (Sterlitech) to allow for exchange of dissolved oxygen, media, nutrients, and various treatments into the hydrogel with cells.

COMSOL modeling: Concentrator. COMSOL particle tracing was performed to study the cell concentrator. Fluid going into the larger top inlet and fluid with particles going into the top right inlet was modelled. The diagonal line represents a wall of 3 µm pores. The majority of DEP buffer leaves through the pores, while the majority of cells moves through the outlet with hydrogel. Due to a computational error involved with COMSOL treating particle tracing as points in a continuum, a few cells were able to pass through gaps much smaller than the cells themselves. However, in reality this cannot happen.

Figure 7:
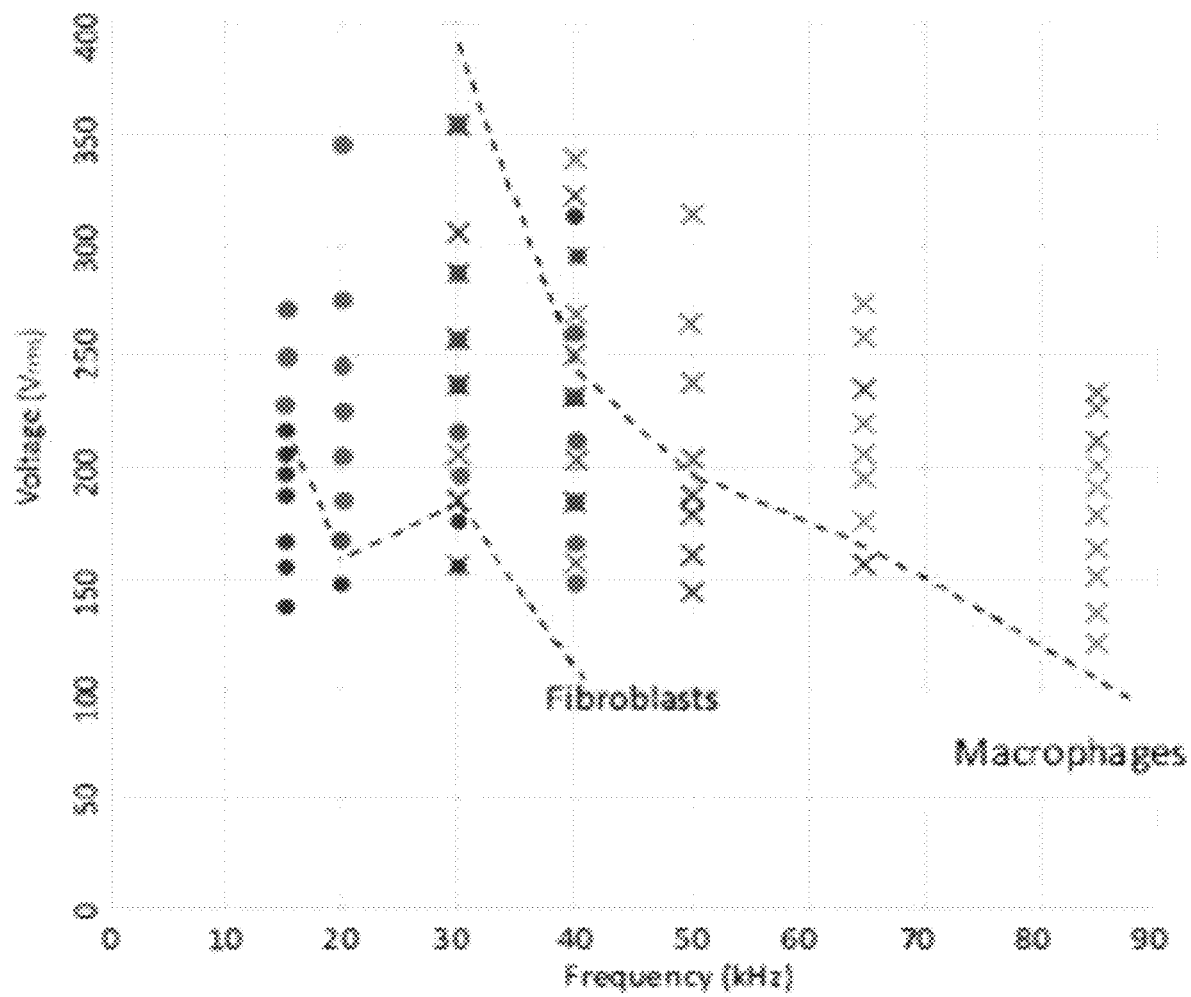
FIG. 7 can show a plot of fibroblast and macrophage trapping ranges.

Cell Separation. This device is envisioned to have multiple purposes. It was previously showed that highly similar cell separation is possible. The downstream section of the device can be used in this case to do chemotherapy optimization, combination therapy, or any kind of study involving diffusing small molecules into hydrogel for interaction with cells in 3D. In a second mode at lower flow rates (about 1 µl/min rather than µl/min about), bulk separation of more distinct cell populations is possible, and could be used to study a variety of cell combinations, including immune system studies, chemotaxis, colocalization and migration, and more. For this reason, we performed a test case in which macrophages and fibroblasts were separated in the DEP device. The results displaying the separability of the two populations are shown in FIG. 7, while trapping ranges for each are found in FIG. 7. Without being bound by theory, excellent separation between the two populations relates to their size as well as the structure of the cells, with fibroblasts being highly elongated in culture, and the macrophages being spherical and nonadherent. It was observed that of the macrophages trapping in the fibroblast range, they appeared to be doublets, or two cells stuck together. Similarly, fibroblasts that did not trap appeared to be dying, as they did not contain as much calcein green and were more faint in the images. After trypsinization, when the fibroblasts are balled up they still retain some of their previous structure in the form of submembrane structure, such as microtubules and actin filaments. We observed an interesting phenomenon at high frequencies, where cells would redirect from their streamlines to the posts, indicating dielectrophoretic trapping, but would release before the voltage was turned off. In FIG. 7, this phenomenon is called transient trapping. This could have been one of several phenomena. Electroporation or loss of viability in response to the high frequencies would cause a change in membrane capacitance which would cause the cells to fall off. However, if the phenomenon were electroporation one would expect the cells to suddenly change their optical properties (a sign the membrane is no longer intact). In addition, at higher voltages of the same frequency, trapping without release was still observed, which, without being bound by theory, would likely not occur if the mechanism of reversible trapping was electroporation. Without being bound by theory, a sub-reversible electroporation could be happening, in which small, transient pores cause a slight change in the intracellular ion concentration, causing the cells to fall off in response to a decreased ion gradient, but then restabilize rapidly. Thirdly, a secondary phenomenon involving the cell response to alternating current could be occurring.

Figure 9:
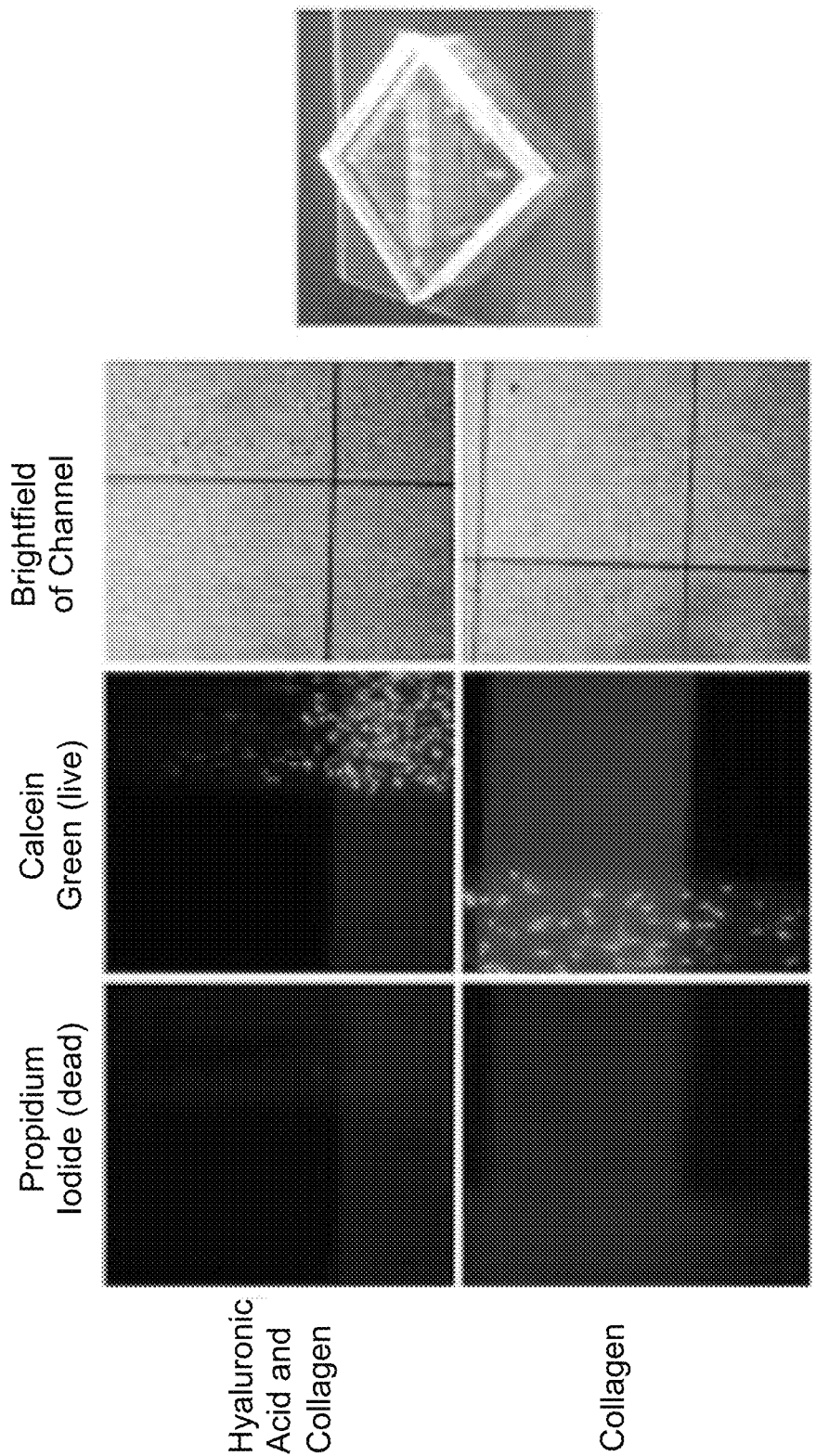
FIG. 9 can show cell viability in microfluidic chips 24 hours after incubation. Collagen and HA/Collagen matrices shown.

Cell Viability. To test cellular morphology and survival in a comparable system, a study using a smaller chip design [Bonakdar] was used to analyze the viability the brain tumor cell line, U251, cultured in a Hystem-C hyaluronic hydrogel matrix and low density 2 mg/ml collagen matrix, separated by a semipermeable membrane with 4 um pores from a nutrient media. The results are shown in FIG. 9. In the hydrogel directly under the membrane, the Hystem-C matrix appeared to provide the cells with a slightly better growth condition, as the cells seemed to elongate more. However, viability was high in both the Hystem-C (hyaluronic acid gel) and the collagen matrix. Hystem-C was selected for further studies because in testing, collagen tends to gel while going through the serpentine, making laminar flow impossible.

Figure 10A:
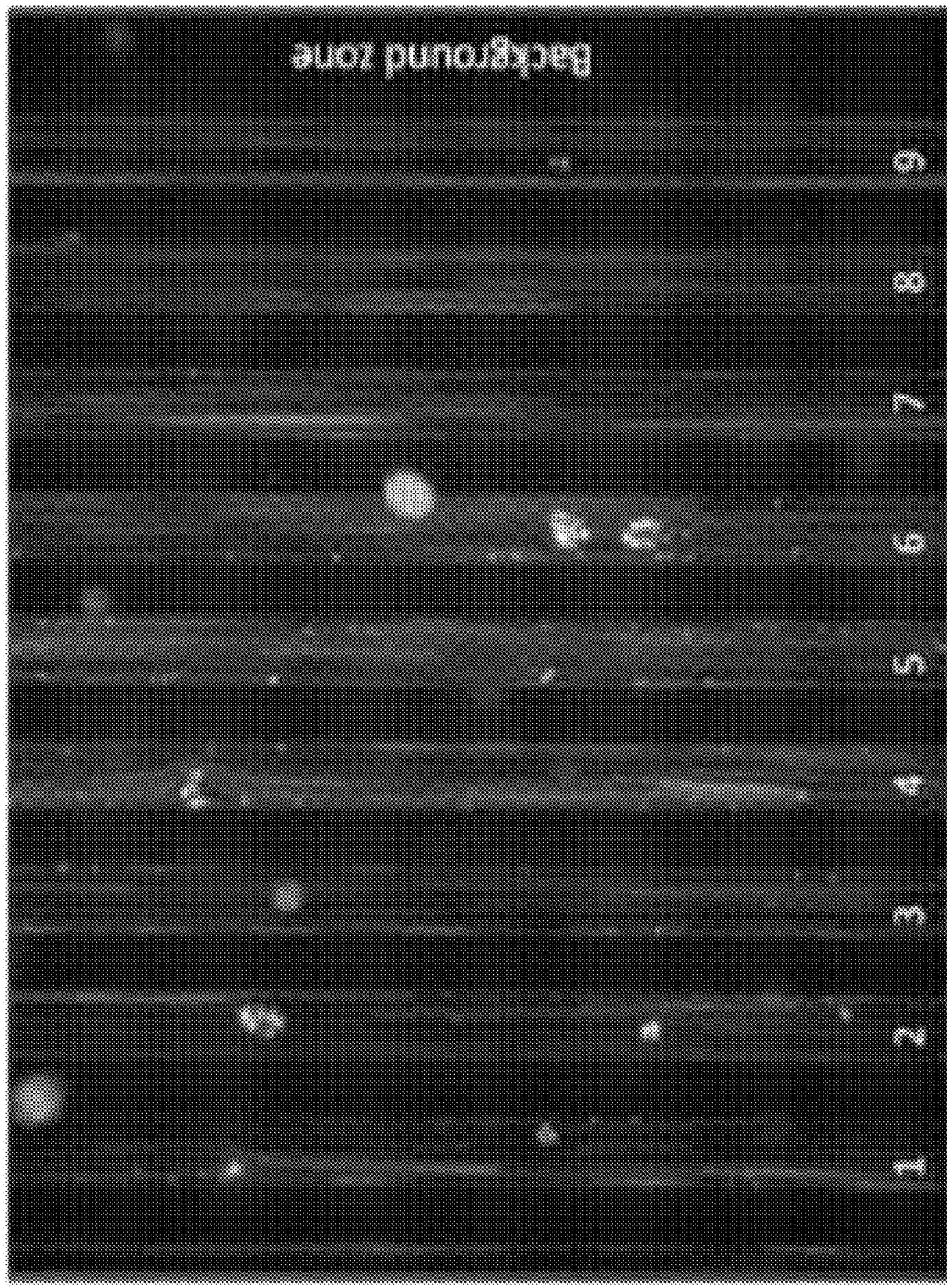
Figure 10B:
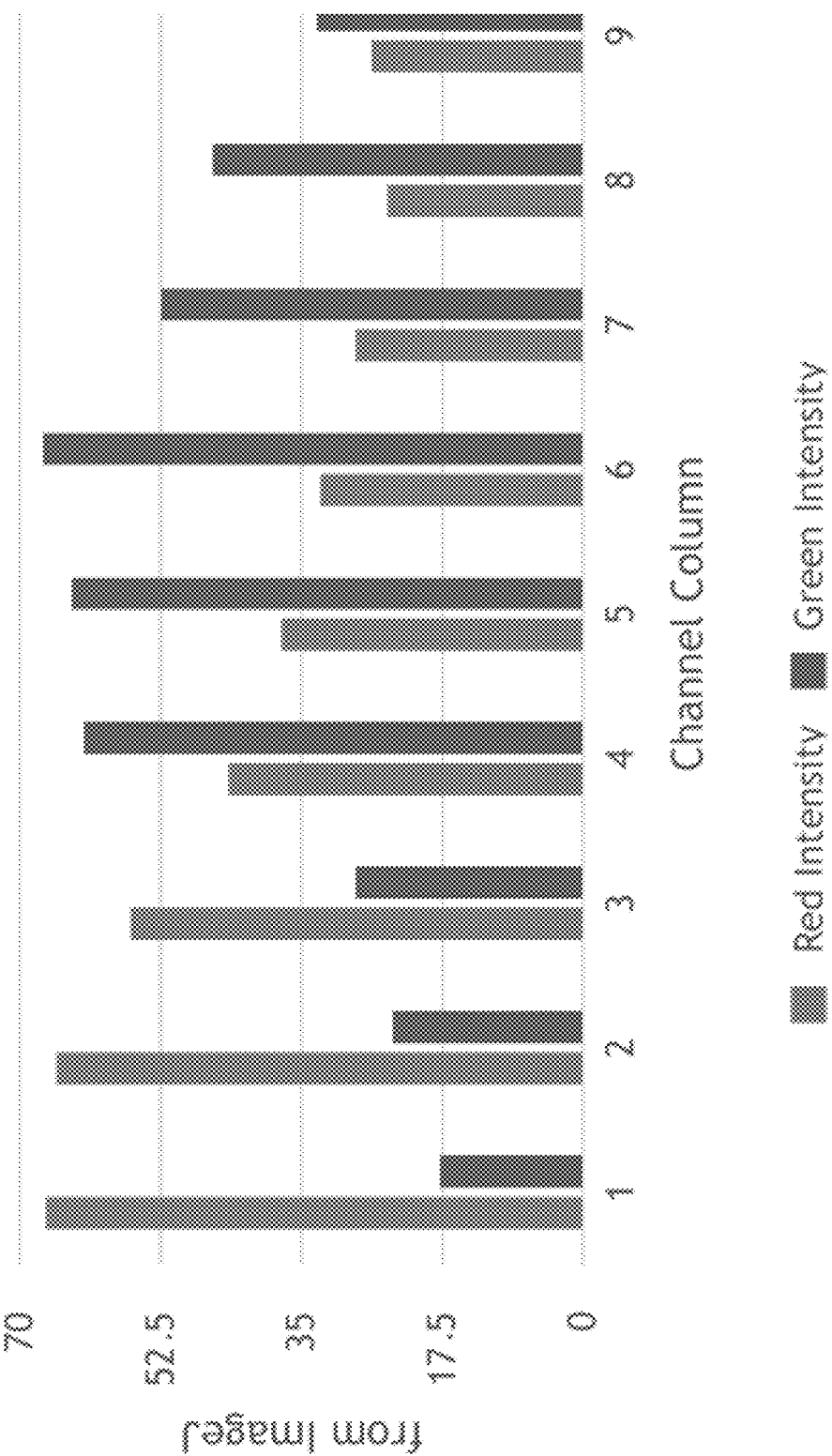

Plug flow maintenance. In FIG. 9, red and green cells were flown through the device. Uncured low-density collagen was used as the medium for the cells. While plug flow was mostly maintained, it was observed that the collagen seemed to start curing while flowing through the device, creating small balls of multiple cell types as different cells flowed past. In addition, because collagen cures at room temperature and in the microfluidic device it quickly approached room temperature, this process seemed to be accelerated. Because of this, the system was switched to Hystem-C, a hyaluronic acid-based 30 matrix gel that cures at 37° C. Initial studies with Hystem-C show that it does not create islets. In addition, due to issues related to pressurization, the syringe pump would not push fluid through the device at a constant rate, so the flow rate of 10 nl/min was taken as a reference value. This section of the chip was modified to have wider channels, with an aspect ratio still high enough to maintain plug flow and a larger width to reduce channel pressurization. Results are shown in FIGS. 10A-10B.

Materials and Methods.

Fabrication: DEP Separation chip. Fabrication of the cDEP chips has been previously described in detail.

Fabrication: Concentrator and Serpentine Chips. The cell concentrator and cell culture chamber were fabricated using well-established microfabrication techniques for PDMS. The concentrator was manufactured using deep reactive ion etching (Bob Geil, UNC) on a silicon wafer using a soda-lime mask (Photo-Sciences). It has a channel height of 100 um. The two layers for the serpentine channel were produced using standard SU-8 manufacturing (MicroChem) with a height of 100 um on a silicon wafer (University Wafer). The wafers were then silanized to improve hydrophobicity and avoid PDMS sticking. Sylgard-184 polydimethylsiloxane (PDMS), mixed in a ratio of 10:1 w/w base to cross-linker, was degassed and cast molded in the two serpentine channel molds and one concentrator mold. 0.75 mm holes were punched for inlets and outlets. The concentrator layer was plasma bonded to a glass slide and placed in a vacuum until use.

To bond the two layers of the serpentine channel separating them with a 0.4 um permeable membrane (Transwell), the following procedure was used. First, PDMS was mixed with toluene in a 1:1 w/w ratio and spin-coated on a glass slide. PDMS layers, previously kept in vacuum for at least 15 minutes, were immediately placed pattern-side down on the glue and kept in contact for 1 minute to ensure good coverage of the clue with the PDMS layers. Carefully, the PDMS layers were removed from the glass slide. The permeable membrane, previously cut to size, was aligned on the bottom layer. The top layer was then aligned over the membrane and bottom layer to complete the bonding. The devices were cured at room temperature for 48 hours in order to allow the liquid PDMS to cure. Punching using a 0.7 5um punch was performed at appropriate intervals. After curing was complete, the devices were bonded to a glass slide.

Cell Preparation. U251 human glioblastoma cells were cultured in DMEM with 10% FBS (Atlanta Biologicals), 1% penicillin-streptavidin, 1% non-essential amino acid and 1% sodium pyruvate. Cells were grown in adherent dishes and routinely passaged at 80-90% confluence. OP9 Human fibroblasts were cultured in MEMalpha with 20% FBS, 1% penicillin-streptavidin, and 3.4 g/L sodium bicarbonate. They were grown in adherent dishes and passaged when they reached 70% confluency. Mouse macrophages PMJ2-R (ATCC® CRL-2458™) were grown in low adherence dishes in a medium of DMEM with 5% FBS, 1% penicillin-streptavidin, and 3.4 g/L sodium bicarbonate. They were passaged by direct splitting, and dead cells were cleared using a 40 um cell strainer (live cells grow in clumps).

Viability Testing in HA and Collagen. To quantify the long-term viability and phenotype of cells cultured in the downstream chamber, we performed a viability experiment in two commercially available hydrogels: Type-I Collagen (Cell Applications Cat #124-25) mixed to a density of 2 mg/ml and HyStem-C (ESI-BIO). Viability experiments were performed in a simplified microfluidic setup: a permeable polyester membrane (0.4 um pores, Transwell) separated a single upper channel from six, lower channels oriented perpendicularly to the top channel. For the experiments, cells suspended in hydrogel were loaded into the lower channels and media was supplied to the cells statically via the upper channel. A confluent flask of U251 cells was trypsinized, and the cells were centrifuged and stained with ca Ice in green (Thermo Fisher). Collagen (Type I rat tail 2 mg/ml) and HyStem-C hydrogel (0.25:4 cross-linker to base), prepared according to manufacturer's instructions, were used to suspend the stained cells. Cells in the uncured hydrogel were loaded into the bottom channels of the device where the hydrogel was cured. The microfluidic devices were incubated at 37° C. and imaged at 1 hr, 2 hrs, and 24 hrs post-curing to determine cell viability and phenotype. 30 minutes prior to the first imaging, Propidium Iodine (20 mg/ml) and calcein green (Sug/ml) was added to the upper channel to stain nonviable cells. Two experiments for each hydrogel type were performed. Collagen (Cell Applications Cat #124-25 rat tail collagen 4 mg/ml) was prepared by Collagen was mixed according to a protocol found at Gibco, Publication Number MAN0007327, and altered slightly for our application. The total volume of collagen used was 0.5 ml, with base collagen volume of 250 µl, a 10×DMEM volume of 50 ul, a 1N NaOH volume of 6.25 µl, and a DI water volume of 193.75 µl. We mixed the water, sodium hydroxide and IOx DMEM on ice. Then we added the collagen. The final color was a slight pink. Liquid collagen was loaded into microfluidic devices and wells, and was cured in the cell incubator at 37° C. HystemC (Esi bio Cat: GS312) hydrogel was prepared according to the manufacturer's instructions in a 0.25:4 v/v cross-linker to base ratio.

Experiment to determine degree of plug flow mixing in collagen. U251 cells were stained red and green before the experiment. Cells were mixed with low density collagen, 2 mg/ml. A serpentine channel was prepared and cells were flowed in at a flow rate of I0 nL/min. When the red plug was in the channel, tubing was switched to send green cells mixed in collagen. As the flow is primarily pressure driven, stopping the flow rate only slowed cell movement so images were taken of moving cells.

COMSOL Multiphysics Modeling. Finite element modeling of the cell concentrator was perfumed using COMSOL Multiphysics 5.2. COMSOL's Laminar Flow Module and Particle Tracking Module were used to simulate flow in the concentrator and the movement of cells.

Showing DEP Separability of subpopulations in a system: Macrophages and Fibroblasts. Several experiments were completed using single-channel DEP chips. For each experiment, a DEP chip was fabricated and left under vacuum for at least 24 hours. Before beginning, the chip was primed with ethanol (see previous articles for further detail [Jaka]), then DEP buffer (8.5% sucrose [w/v], 0.3% glucose [w/v], 0.725% RPMI [v/v]). Cells were prepared by staining with calcein green or red (at 5 ug/ml each) for 15 minutes, then they were trypsinized, and moved to a 15 ml falcon tube. The cells in media were mixed with DEP buffer with 0.1% w/v BSA, 0.1 mM EDTA and 0.1% w/v Kolliphor P188 (jaka], to a final volume of 10 ml with, and were centrifuged at 120 g. Following centrifugation, the cell pellet was resuspended in DEP buffer with BSA, Kolliphor P188 and EDTA to a volume of 10 ml, and the centrifugation was repeated. After the second centrifugation, cells were resuspended in 1 ml of simple sterile DEP buffer, and conductivity was tested. A small sample was taken for viability analysis was stained with Trypan blue and counted on the hemocytometer. In initial experiments, macrophages and fibroblasts were independently run through the chip. For a range of frequencies, the applied voltage was turned up in regular intervals to the maximum possible with the current amplifier. At each frequency/voltage pairing, if trapping on posts was observed, the voltage was pulsed on and off to observe reversibility of trapping. Irreversible trapping (where the cells did not leave the post after the voltage was turned off) was not considered active DEP trapping. In a later experiment, fibroblasts and macrophages were stained green and red, respectively. They were then run through the device together at a flowrate, voltage, frequency combination that was shown to be between trapping frequencies for the two cell lines.

Cell tracking Software. An ImageJ algorithm was written to determine percentage of cells trapping in device at a given point in time. This algorithm is operated as a macro. The algorithm thresholds the image into black blobs on a white background, and then using the watershed filter to separate clumped cells into individual units. Then the macro samples a user-instructed number of files. For each pixel, the program determines in those files whether it was 1 (black) or 0 (white). If it determines that in the selected frames there were 1's and 0's (the cell moves), the program writes it in a new file as 0 (white, no cell). If the frame has all 1's (the cell did not move), it is written in a new file as a 1 (cell). In the output the user then obtains a video with all cells, moving and stationary, and a video with only stationary cells. The program then uses the ImageJ cell counter plugin to count the net number of cells in each frame and stationary cells in each frame.

Example 2

Introduction.

Cancerous tissue is heterogeneous in nature, often containing several subpopulations of cells with varying degrees of aggressiveness and susceptibility to different types of chemotherapy. Currently, cancer treatment tends to treat the bulk of a tumor, often leaving behind treatment-resistant cells that can then repopulate the space, during which they evolve in a new microenvironment, leading to treatment resistance and recurrence. Despite numerous studies, the complexity of determining which treatments will be most effective in different scenarios is still unsolved, with some evidence showing that unoptimized application of chemotherapy can mutate the surviving cells, which can increase heterogeneity and in turn lead to the emergence of more aggressive and metastatic subpopulations. In particular, attempts to treat metastatic cells often fail, leading to death in many cases. One particularly worrisome aspect during tumor evolution is the development of metastatic subpopulations. Research has shown that the epithelial-to-mesenchymal transition (EMT), the process by which cells obtain traits that increase their ability to migrate, is crucial in this process and involves single-cell evolutionary processes. We hypothesize that a necessary-and-sufficient aspect of this transition involves changes to the structure of the cell membrane that allow the cell to migrate and to pass through capillary walls to circulate and move to other sites, with this behavior correlating with the EMT.

Contactless dielectrophoresis (cDEP) is a technique that uses an applied AC electric field to induce cellular polarization in a microfluidic device containing an array of cell-sized posts. These posts are insulative: the electric field gradient induced around the posts causes cells to migrate toward the posts and trap if the electric field is on. Cellular polarization in dielectrophoresis is frequency-dependent and is dependent on cellular characteristics. Therefore, only some cells will trap if their bioelectrical phenotype allows polarization at a certain frequency and the force on the cell outweighs the Stokes drag force on the cell.

Dielectrophoresis theory suggests that changes to the structure of the cell membrane can change the frequency at which a cellular dipole is induced. By this logic, changes in the structure of the membrane correlating with the EMT should be quantifiable using low-frequency contactless dielectrophoresis. It has been shown that using cDEP, mouse ovarian surface epithelial cells at different stages of malignancy can be separated with DEP, while also retaining high viability. This indicates potential for the device to separate tumor subpopulations for further characterization.

Without being bound by theory, the development of a multistage cDEP device can improve chemotherapy selection by allowing for morphologically unique cells to be separated based on their electrical polarizability and tested separately against an array of chemotherapies. Without being bound by theory, changes in the structure of the cell membrane correlating with EMT are a major contributor to this difference in cellular trapping. Having a downstream cell culture device would a) allow validation studies on this correlation to be performed in a rapid and re-producible way, and b) provide a method for systematically studying bioelectrically distinct tumor subpopulations for markers in 3D culture: cellular aggressiveness, motility, growth rate and response to chemotherapy, immunomodulatory molecules, or anything else that can be diffused in hydrogel.

This device can be used as follows: upon receiving a tumor biopsy, cells flow through the dielectrophoretic cell separator where they are separated by their subtype, flow through a system that transfers them to uncured hydrogel, and then flow into a culture chamber where they can be cultured in 3D as an indicator of metastatic capacity. This is followed by testing chemotherapy (or other) agents against each cell subtype individually. Using these data (for each subtype, growth rate, malignancy and susceptibility to a panel of chemotherapies or other treatments). This single-chip device can also be paired with a computer algorithm that can model optimum treatment regimens based on output data.

Theory and Modeling. The theory and Modeling is also discussed in Example 1. Neutrally charged lossy particles and cells exposed to an inhomogeneous electric field experience a dielectrophoretic force (Eq. 1):

$$\vec{F}_{DEP} = 2\pi\varepsilon_m r^3 ReK(\omega)\nabla|\vec{E}_{rms}|^2 \qquad (Eq.\ 1)$$

Here, r is the radius of the cell, $\vec{E}_{rms}$ is the root mean square of the electric field, is the $\varepsilon_m$ is the permittivity of the medium, and $K(\omega)$ is the Clausius-Mossotti factor. The Clausius-Mossotti factor is describe by Eq. 2, $$(\varepsilon^*_p - \varepsilon^*_m)/(\varepsilon^*_p + 2\varepsilon^*_m) \qquad (Eq.\ 2)$$

where $\varepsilon^* = \varepsilon + i\sigma/\omega$ (Eq. 3), with $\varepsilon^*$ the complex permittivity, $\varepsilon$ the permittivity, $\sigma$ the conductivity, and $I = \sqrt{-1}$ (Eq. 4). The subscripts p and m represent the particle and medium, respectively. The dielectrophoretic force can thus be used to separate cells based upon their radii, the dielectric permittivity of the cells, and the frequency of the applied voltage. By tuning the frequency of the applied voltage, the cDEP chip can attract and trap a subpopulation of the cells to the insulated posts while other subpopulations are repelled. In addition to the dielectrophoretic force, cells in a DEP chip also experience the drag force, which balances with this DEP force to optimize trapping.

Downstream of the cDEP chip, the cell concentrator is designed to concentrate the cells in a smaller amount of low conductivity DEP buffer while simultaneously exchanging the low conductivity buffer used in the DEP experiments with uncured hydrogel. This design accomplishes these two tasks using a diagonal wall with small pores that acts as a sieve. The small size of the pores prevents cells from passing through the wall and forces cells to move along the edge of the porous wall into an outlet. Because the wall of pores has a higher net cross-sectional area than a secondary outlet, the low conductivity DEP buffer exits the device while the cells are mixed into the hydrogel before reaching the outlet. This device allows the system to be fully microfluidic, avoiding cumbersome centrifugation steps in order to move the cells from DEP buffer to hydrogel, and potentially compromising sterility. A labeled schematic of this device is shown in FIG. 11.

Experimental Models.

Chip Fabrication. The mold for the concentrator along with 7 other variations on the pattern were fabricated using deep reactive ion etching on a silicon wafer using a soda-lime mask (Photo-Sciences). The channel height is 95 μm. The wafer was silanized to improve polymer lift-off. To make the chip, Sylgard-184 polydimethylsiloxane (PDMS) was mixed in a ratio of 5:1 w/w base to cross-linker, was degassed and cast molded. The increased ratio of cross linker (compared to 10:1) was used to increased stiffness so that the posts in the chip would not collapse. The chip was cured for 1.5 hours at 150° C. The longer and hotter curing time was chosen to also increase material stiffness. Immediately upon removing the PDMS from the mold, 0.75 mm holes were punched for inlets and outlets and the chip was plasma bonded to glass. The chip was not cleaned with tape as this will damage the fragile posts. The concentrator layer was plasma bonded to a glass slide and placed in a vacuum until use.

Choice of Hydrogel. Several hydrogels were selected and tested during this process. We observed that very high viscosity hydrogels can damage fine microfluidic features and/or fail to load into a chip. In addition, bubble formation in higher viscosity gels is nearly impossible to resolve. Gels that cure rapidly or cure in response to temperature are also not good candidates, as gelation occurs at nucleation sites and does not occur uniformly. This makes loading a microfluidic device nearly impossible. For this reason, Glycosil (ESI-BIO) was chosen as it cures very slowly over a 24 hour period with eventual autocrosslinking. It is a hyaluronic acid hydrogel that when resuspended creates a 1×PBS environment, making it a good candidate for mixing with cell media and flowing into a device for further diffusion of media into the gel.

Testing Particle Concentration. Before running an experiment, the chip was left 2 hours under vacuum to degas. To load the chip, there must never be a high surface tension within the device, as this will damage the posts. Therefore, the chip was primed first with ethanol, then with DI water, before adding the hydrogel. To test cellular motion within the device for comparison with COMSOL modeling results, 15 um red labeled polystyrene beads (Invitrogen) in DI water were flown in through the cell/DEP buffer inlet. 15 μm blue beads (Invitrogen) in DI water were mixed 1:1 with Glycosil (ESI-BIO) and flown in through the hydrogel inlet. Blue beads were used as a way to trace the motion of the hydrogel in the device, even though they cannot go through the pores. Each mixture was loaded into syringe pumps. First, buffer was flown in at 1 μl/min until the chip was loaded with beads. The buffer feed speed was then increased to 2 μl/min until there was sufficient effluent at the outlets. This effluent was collected and the volume was measured. A hemocytometer was used to count the number of red/blue beads in the output.

Testing Buffer Siphoning. To test the mixing of different subpopulations in the chip, DI water was run into the channel DEP buffer/cell inlet, and 1×PBS mixed with the prepared glycosil was run into the hydrogel inlet. The chip was primed with ethanol, then DI water. The buffer solutions were loaded into 1 ml syringes, attached to syringe pumps (Harvard), and connected to the chip. A flow rate of 2 μl/min was used through each of the inlets. Short pieces of empty tubing (PTFE 22 gauge) were attached to the outlets and buffer ran out into these. When the tubes were about ⅔ full, they were removed from the chip and the fluid was unloaded into a microcentrifuge tube. This outlet fluid was mixed to make a 12.5% outlet solution in DI water. The conductivity of these solutions was measured with a conductivity meter.

Results.

FIGS. 12A-12E show the result of particle flow through the chip. The flow was stopped to image the distribution of particles in the chip. 15 μm blue beads were used in the inlet with hydrogel to help visualize flow, and 15 μm red beads were input in the other inlet. The beads for the most part did not pass the semi-permeable wall but flowed out the device. Some particles stuck in the grate of the device, but it may be possible to alleviate this by optimizing flow rate to enhance inertial effect of the beads.

Figure 14:
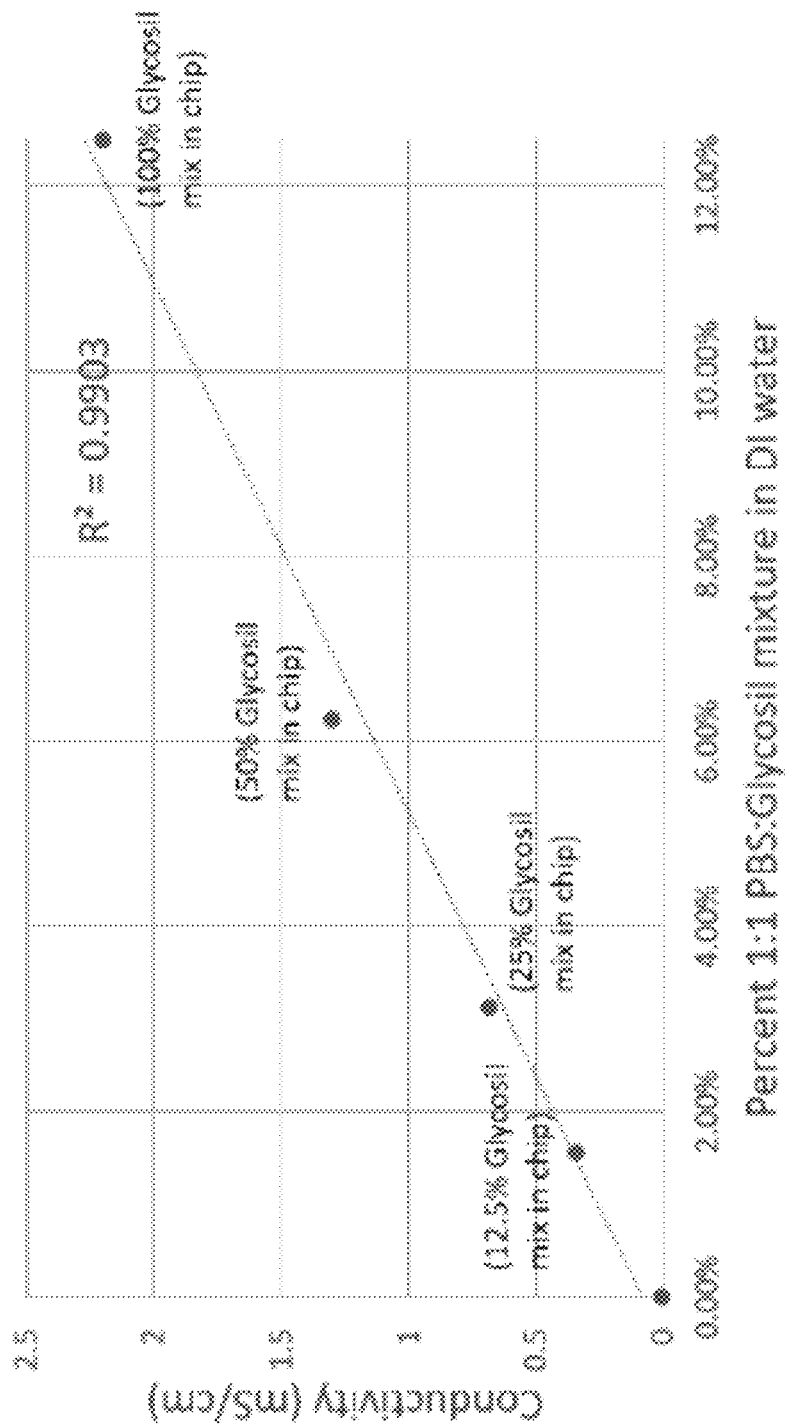
FIG. 14 shows a conductivity curve for 1:1 glycosil:PBS mix in DI water. As experimental outputs were in small volume, they were mixed with DI water at a ratio of 12.5% to produce larger volumes for conductivity reading. The numbers in parentheses represent the percent of glycosil mix that would correspond with the above conductivity mapping. As the other solution in the chip was DI water, the percent DI water in a chip output solution can also be calculated using this graph.

At the output of the device, beads were collected and counted using a hemocytometer. 8 μl of fluid came out each outlet indicating relatively equal fluid output. Counts from each outlet are shown in the table in FIG. 13. In the conductivity experiments, conductivity was measured in the output solutions (a mixture of 1:1 glycosil:PBS and DI water flown into the chip) mixed with 12.5% DI water. A mapping of these conductivity values to what would be the percent mixing are shown in FIG. 14. Using this linear regression, the following equation was developed to correlate percent mixing in the chip with measured conductivity of the 12.5% solution (Eq. 5):

Fraction glycosil mix in chip output=(Conductivity [mS/cm]−0.0852)/2.186 (Eq. 5)

The conductivity of each of the outlets is shown in FIG. 15. The conductivity of DI water is 4 μS/cm, whereas the conductivity of the 1:1 Glycosil-PBS mixture is 16.8 mS/cm. Some variability exists in the output populations, as would be expected, with some degree of flow instability in the chip.

This device can be used as part of an integrated system for personalized tumor diagnostics, in which each subpopulation in a patient's biopsy is separated by their dielectric signature. Following separation, these subpopulations can be embedded in hydrogel to assess proliferation capacity, aggressiveness, and sensitivity to a panel of chemotherapeutics. This can allow for a more combinatorial approach for chemotherapy selection, where information on cell aggressiveness, growth rate, and response to chemotherapies can be assessed simultaneously. Hyaluronic acid hydrogels have begun to be characterized as an in vivo material, and could provide a unique cellular environment compared to collagen.

This chip can be used to gather data on the correlation be-tween specific trapping frequencies and regular phenotypic information. It has been observed that lower trapping frequency within a cancerous cell type tends to correlate with metastatic capacity, which we hypothesize is due to changes in the structure of the cell membrane before migration. These changes can be observed in the number and form of pseudopodia and in the dysregulation of cell morphology. Current DEP theory does not account for such structural and morphological changes, and with a large database of this information, as well as information on treatment resistance and malignancy, we hope to solve the problem of identifying which cellular properties correlate with specific bioelectrical phenotypes and frequency-dependent states.

Serpentine Development.

Downstream of the concentrator presented in Chapter 5, we are developing a serpentine channel separated from a panel of chemotherapies or small diffusible molecules, separated by a membrane with 0.3 μm pores. An image of this is shown in FIG. 16. Once cells are flown into the serpentine and the gel is cured, chemotherapies can be diffused across the membrane with media to test each subpopulation against an array of therapies. Initial work on this has focused on changing the bonding parameters to ensure a seal between the PDMS and the membrane, changing serpentine channel sizes to minimize the pressure differential across the chip while maintaining separate populations in the device. Alternative techniques could include microfluidic valve systems to multiplex cell batches into separate wells or mechanically moving output tubing into a 96 well plate rather than relying on fluidic methods.

Example 3

Many sophisticated mathematical models for tumor growth have been developed over the years. However, there is often a disconnect between model development and the translation of this information back into the clinic. Without being bound by theory, by using data obtained off the dielectrophoresis microdevice such as subpopulation morphology, aggressiveness, and response to treatment, a simple mathematical system can be developed that can be optimized to predict chemotherapy outcomes based on data obtained off chip and a model of cell-cell interactions and response to treatment. An example model system that could use data obtained using the chip for all parameters is shown below.

In this model, all numbers are normalized to show general trends that could be shown using the device, but these models do not reflect actual data. These represent a simplified model that could be elaborated for use.

A set of differential equations for the change in number of cells of subpopulation i in a theoretical tumor was first developed:

$$\frac{dP_i}{dt} = r_i P_i \left(1 - \sum P_i\right) - \epsilon_i P_i X \qquad \text{(Eq. 6)}$$

For example, in a theoretical tumor with only two subpopulations (one can also imagine a tumor in which all subpopulations are divided into two groups with more or less similar properties), the populations would be $P_1$ and $P_2$ and the set of differential equations would be:

$$\frac{dP_1}{dt} = r_1 P_1 (1 - P_1 - P_2 - P_3) - \epsilon_1 P_1 X \qquad \text{(Eq. 7)}$$

$$\frac{dP_2}{dt} = r_2 P_2 (1 - P_1 - P_2 - P_3) - \epsilon_2 P_2 X \qquad \text{(Eq. 8)}$$

$$\frac{dP_3}{dt} = r_3 P_3 (1 - P_1 - P_2 - P_3) - \epsilon_3 P_3 X \qquad \text{(Eq. 9)}$$

Here, $\epsilon_i$ is the chemotherapy kill rate for population i, $P_i$ is the number of cells in population i, $r_i$ is the birth rate minus the natural death rate for population i (so net growth over time in absence of chemotherapy) and X is the drug concentration as a piecewise function in time, to account for both dosage and timing.

Due to the piecewise nature of X, this equation becomes very difficult to study from a theoretical point of view, and would require the use of impulse differential equations, a topic covered in. Fortunately, the use of numerical methods for resolving time-dependent differential equations has become much easier in recent years with the development of MATLAB.

For example, for the initial case scenario (no spatial dependence or evolution in time), one can plot a tumor with 3 phenotypically unique subpopulations. One chemotherapy is applied at a finite dosing period, and the three cell populations respond differently. The parameters are normalized to be unitless. For this model, the normalized parameters are shown in FIG. 17.

Figure 18:
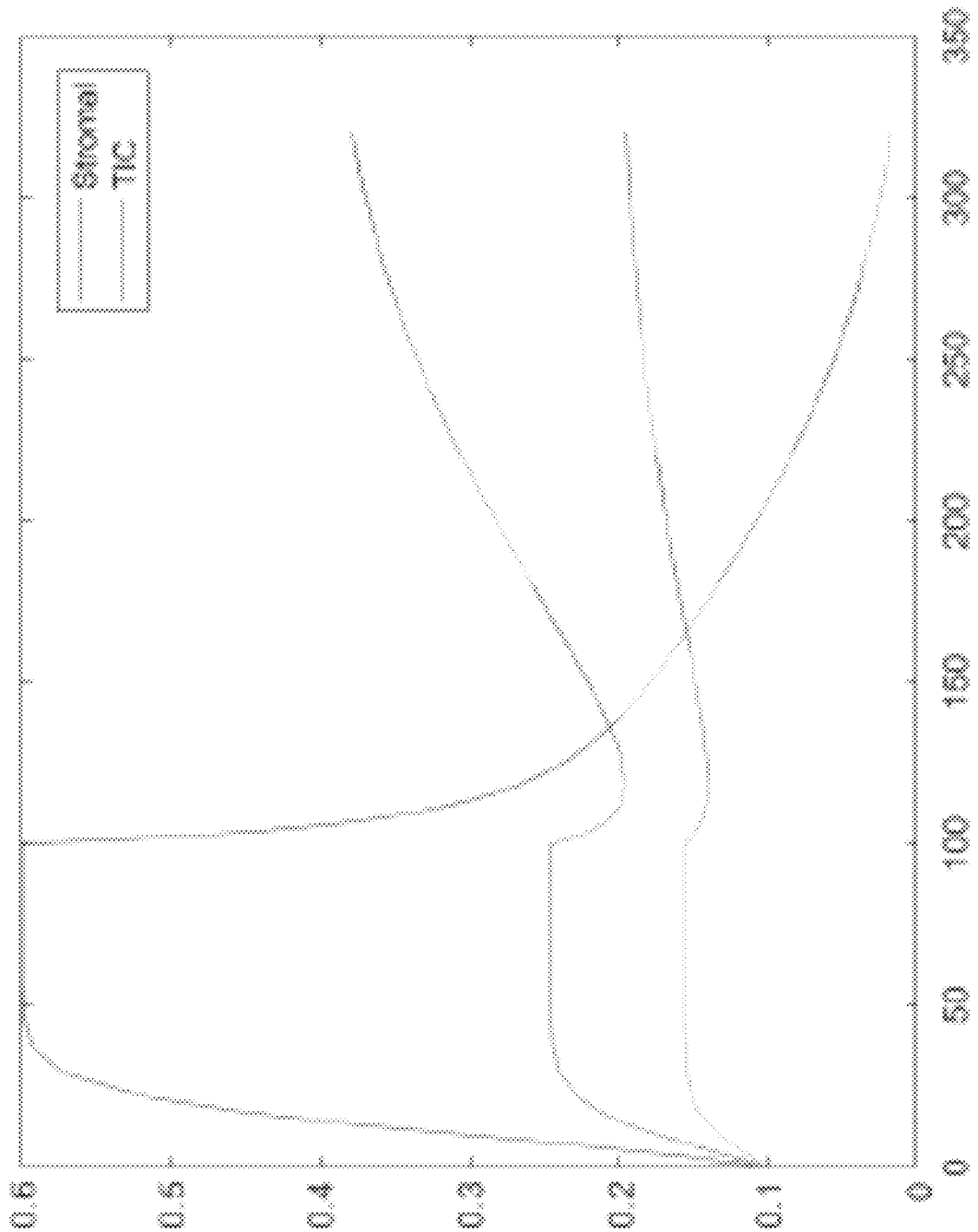
FIG. 18 shows a theoretical model of a system of 3 subpopulations undergoing continuous treatment after an initial growth period, with normalized parameters.
Figure 19:
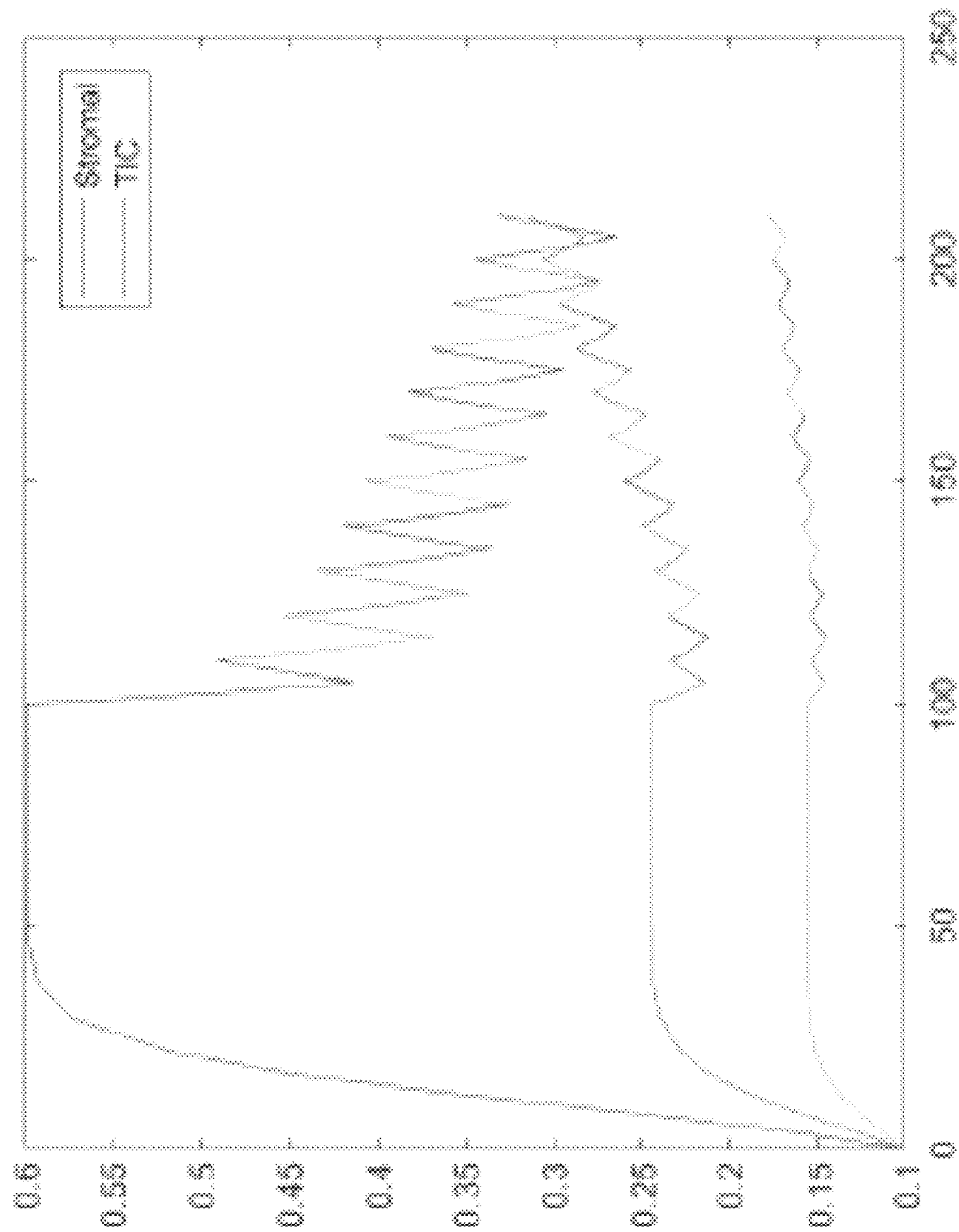
FIG. 19 shows a theoretical model of a system of 3 subpopulations undergoing periodic treatment (i=10) after an initial growth period, with normalized parameters.
Figure 20:
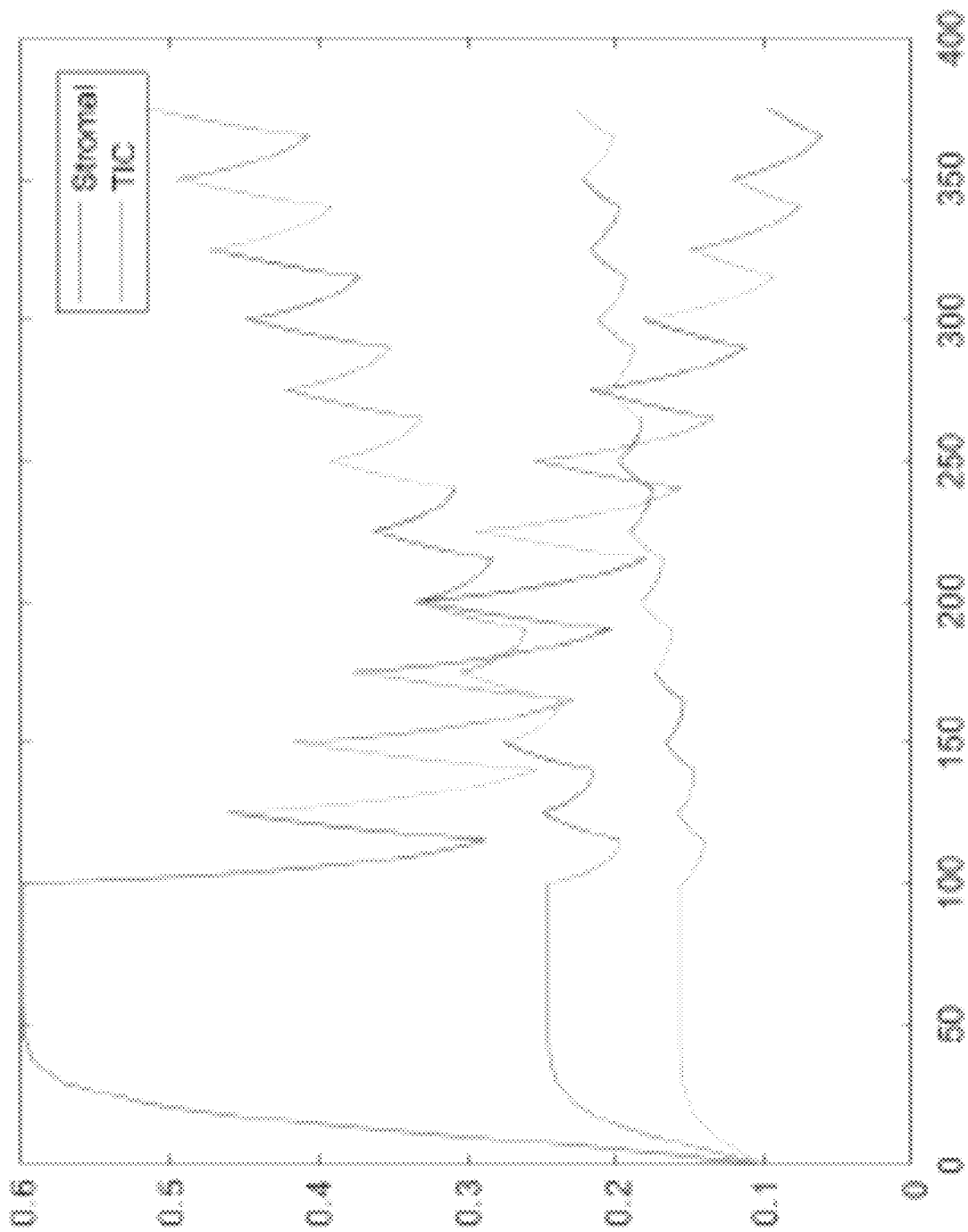
FIG. 20 shows a theoretical model of a system of 3 subpopulations undergoing continuous treatment (i=25) after an initial growth period, with normalized parameters.

Using the MATLAB codes provided, this can be written for an arbitrary number of cell subpopulations. Using this system, we could potentially predict many different treatment outcomes. Randomizing this model allows one to take into account stochastic variability in growth, a first-order approximation for spatial dependence. The model can be expanded to account for cellular evolution and take data from the device described here and elsewhere herein. In addition, the growth model can be modeled as Gompertzian growth, a more accurate representation of tumor growth which takes into account fractal-like boundaries rather than as a logistic curve. FIG. 18 shows a theoretical model of a system of 3 subpopulations undergoing continuous treatment after an initial growth period, with normalized parameters. FIG. 19 shows a theoretical model of a system of 3 subpopulations undergoing periodic treatment (i=10) after an initial growth period, with normalized parameters. FIG. 20 shows a theoretical model of a system of 3 subpopulations undergoing continuous treatment (i=25) after an initial growth period, with normalized parameters.

We claim:
1. A microfluidic separation and assay system comprising:
   a microfluidic contactless dielectrophoretic (cDEP) device, wherein the microfluidic cDEP device comprises:
      a cDEP main chamber comprising a main channel layer and an electrode layer comprising electrode channels, wherein the main channel layer and the electrode layer are separated by a cDEP membrane, and wherein the main channel layer comprises a plurality of pillars;
      a cell suspension inlet microchannel, wherein the cell suspension inlet microchannel is coupled to the main channel layer,
      an electrode buffer inlet microchannel, wherein the electrode buffer inlet microchannel is coupled to the electrode channels;
   a microfluidic concentrator, wherein the microfluidic concentrator is coupled to the microfluidic cDEP device, wherein the microfluidic concentrator comprises:
      a concentrator main chamber comprising:
      a first inlet configured to receive a fluid flow from the microfluidic cDEP device;
      a second inlet configured to receive an uncured hydrogel;
      a porous wall extending diagonally along a length of the concentrator main chamber and across a width of the concentrator main chamber, wherein the first inlet and the second inlet are on a first-side of the porous wall;
      a first outlet and a second outlet, wherein the first outlet and the second outlet are position on an end of the concentrator main chamber opposite the first inlet and the second inlet, wherein the first outlet and the second outlet are on opposite sides of the porous wall from each other, and wherein the first outlet is on the first side of the porous wall; and
   an assay chamber, wherein the assay chamber is coupled to the microfluidic concentrator and wherein the assay chamber comprises:
      a serpentine microchannel comprising an inlet and an outlet, wherein the inlet of the serpentine microchannel is coupled to the first outlet of the concentrator main chamber via a microchannel;
      a test microchannel, wherein the test microchannel is positioned relative to the serpentine microchannel such that a fluid flow through the test microchannel is perpendicular to a fluid flow through the serpentine microchannel; and
      an assay chamber a porous membrane, wherein the assay chamber porous membrane is positioned between the serpentine microchannel and the test microchannel.
2. The microfluidic separation and assay system of claim 1, wherein the microfluidic cDEP device, the microfluidic concentrator, and the assay chamber are contained on a single microfluidic chip.
3. The microfluidic separation and assay system of claim 1, wherein the microfluidic cDEP device, the microfluidic concentrator, the assay chamber, or a combination thereof are coupled to a downstream or upstream multi-well assay system.
4. The microfluidic separation and assay system of claim 1, wherein the porous wall comprises pores having a diameter that is less than the size of a cell.
5. The microfluidic separation and assay system of claim 1, wherein the microfluidic cDEP device, the microfluidic concentrator, and the assay chamber comprise polydimethylsiloxane.
6. The microfluidic separation and assay system of claim 1, wherein a width of the serpentine microchannel ranges from 50 μm to 3 mm.
7. The microfluidic separation and assay system of claim 6, wherein a height of the serpentine microchannel ranges from 50 pm to 1 mm.
8. The microfluidic separation and assay system of claim 1, wherein the cDEP main chamber comprises 100 to 20,000 pillars.
9. The microfluidic separation and assay system of claim 1, wherein the electrode channels are configured to attach to a voltage generator.
10. The microfluidic separation and assay system of claim 1, wherein the assay chamber porous membrane comprises pores that have a diameter that ranges from 0.001 pm to 2 pm.
11. A method of using the microfluidic separation and assay system of claim 1, the method comprising:
   (a) suspending cells in a low conductivity buffer to form a cell suspension;
   (b) adding the cell suspension to the cDEP main chamber via the cell suspension inlet microchannel;
   (c) adding an electrode buffer to the electrode channel via the electrode buffer inlet microchannel;
   (d) flowing the cell suspension through the cDEP main chamber and applying a voltage to the electrode channel to trap one or more cells against at least one pillar of the plurality of pillars;
   (e) releasing the one or more trapped cells from the at least one pillar of the plurality of pillars;
   (f) flowing the released one or more cells through an outlet of the microfluidic cDEP device into the concentrator main chamber through the first inlet of the microfluidic concentrator;
   (g) adding the uncured hydrogel to the concentrator main chamber;
   (h) removing the low conductivity buffer from the released one or more cells and uncured hydrogel by passing the low conductivity buffer through the porous wall and out of the concentrator main chamber through the second outlet of the microfluidic concentrator;
   (i) removing batches of uncured hydrogel containing the released one or more cells (plugs) from the concentrator main chamber through the first outlet of the microfluidic concentrator;
   (j) flowing the plugs into the serpentine microchannel;
   (k) curing the hydrogel;
   (l) adding a fluid containing an agent to the test microchannel; and
   (m) allowing the agent to diffuse through the assay chamber porous membrane and contact at least one cell in the serpentine microchannel.
12. The method of claim 11, further comprising the step of detecting or measuring a cell response to exposure to the agent in the at least one cell in the serpentine microchannel.
13. The method of claim 11, wherein the agent is selected from the group consisting of: an organic chemical compound; an inorganic chemical compound; a biologic, a toxin, an element, and any combination thereof.

14. The method of claim 11, wherein the low conductivity buffer is an osmotic pressure balanced solution with a conductivity below 300 µS/cm.

15. The method of claim 11, wherein the electrode buffer is a high conductivity buffer having a conductivity measurement above 1 mS/cm.

16. The method of claim 11, wherein the electrode buffer is a 10× phosphate buffered saline solution.

17. The method of claim 11, wherein the hydrogel is selected from the group consisting of: collagen, matrigel, Hystem-C, glycosil, a hyaluronic acid based gel, and any combination thereof.

18. The method of claim 11, wherein the voltage applied ranges from 0 V to 500V.

19. The method of claim 18, wherein the voltage applied is varied during use.

20. The method of claim 11, wherein the cells are obtained from a biopsy.

* * * * *